US010934565B2

(12) United States Patent
Yocum et al.

(10) Patent No.: US 10,934,565 B2
(45) Date of Patent: Mar. 2, 2021

(54) METHOD OF PRODUCING SUCCINIC ACID AND OTHER CHEMICALS USING FACILITATED DIFFUSION FOR SUGAR IMPORT

(71) Applicant: PTT GLOBAL CHEMICAL PUBLIC COMPANY LIMITED, Bangkok (TH)

(72) Inventors: R. Rogers Yocum, Lexington, MA (US); Andrew Christopher Collard, New Haven, CT (US); Theron Hermann, Arlington, MA (US); Xiaohui Yu, Woburn, MA (US); Wei Gong, Woburn, MA (US)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 0 days.

(21) Appl. No.: 16/588,183

(22) Filed: Sep. 30, 2019

(65) Prior Publication Data

US 2020/0032301 A1    Jan. 30, 2020

Related U.S. Application Data

(62) Division of application No. 14/906,501, filed as application No. PCT/US2014/047696 on Jul. 22, 2014, now abandoned.

(60) Provisional application No. 61/857,300, filed on Jul. 23, 2013.

(51) Int. Cl.
| | |
|---|---|
| *C12P 7/46* | (2006.01) |
| *C12N 15/74* | (2006.01) |
| *C07K 14/195* | (2006.01) |
| *C12N 1/36* | (2006.01) |
| *C12N 15/01* | (2006.01) |
| *C12P 7/44* | (2006.01) |

(52) U.S. Cl.
CPC ............ *C12P 7/46* (2013.01); *C07K 14/195* (2013.01); *C12N 1/36* (2013.01); *C12N 15/01* (2013.01); *C12P 7/44* (2013.01)

(58) Field of Classification Search
CPC .................................. C12P 7/46; C12N 15/74
See application file for complete search history.

(56) References Cited

U.S. PATENT DOCUMENTS

| | | | |
|---|---|---|---|
| 10,006,063 B2 * | 6/2018 | Zhang | ............ C12Y 108/01004 |
| 2012/0220000 A1 * | 8/2012 | Gong | ................... C12N 9/1205 |
| | | | 435/145 |
| 2013/0337519 A1 * | 12/2013 | Dole | ........................ C12R 1/01 |
| | | | 435/145 |

OTHER PUBLICATIONS

Tang et al., Appl. Microbiol. Biotechnol., 97, 2513-2520, 2013.

* cited by examiner

*Primary Examiner* — Maryam Monshipouri
(74) *Attorney, Agent, or Firm* — Oblon, McClelland, Maier & Neustadt, L.L.P.

(57) ABSTRACT

This invention relates to the production of succinic acid and other chemicals derived from phosphoenolpyruvate (PEP) by fermentation with a microorganism in which the fermentation medium contains one or more sugars, and in which one or more of the sugars is imported into the cell by facilitated diffusion. As a specific example, succinic acid is produced from a glucose-containing renewable feedstock through fermentation using a biocatalyst. Examples of such a biocatalyst include microorganisms that have been enhanced in their ability to utilize glucose as a carbon and energy source. The biocatalysts of the present invention are derived from the genetic manipulation of parental strains that were originally constructed with the goal to produce one or more chemicals (for example succinic acid and/or a salt of succinic acid) at a commercial scale using feedstocks that include, for example, glucose, fructose, or sucrose. The genetic manipulations of the present invention involve the introduction of exogenous genes involved in the transport and metabolism of glucose or fructose into the parental strains. The genes involved in the transport and metabolism of glucose or fructose can also be introduced into a microorganism prior to developing the organism to produce a particular chemical. The genes involved in the transport and metabolism of sucrose can also be used to augment or improve the efficiency of sugar transport and metabolism by strains already known to have some ability for glucose utilization in biological fermentations.

13 Claims, 4 Drawing Sheets

Specification includes a Sequence Listing.

METHOD OF PRODUCING SUCCINIC ACID AND OTHER CHEMICALS USING FACILITATED DIFFUSION FOR SUGAR IMPORT

CROSS-REFERENCE TO RELATED APPLICATION

The present application is a divisional of U.S. patent application Ser. No. 14/906,501, which was filed under the PCT on Jul. 22, 2014, and which claims priority from U.S. provisional application 61/857,300, which was filed on Jul. 23, 2013.

FIELD OF THE INVENTION

The present invention is in the field of producing specialty and commodity organic chemicals using biocatalysts (bacteria and other microorganisms) that can be modified to increase their efficiency in using sugar-containing feedstocks. More specifically, the present invention is related to the genetic modifications of genes that encode functions involving transport and metabolism of sugars for the biological production of succinic acid and other chemicals.

BACKGROUND OF THE INVENTION

A large number of organic chemicals are currently derived from petrochemical feedstocks. There is a growing interest in producing many of these petrochemical-derived organic compounds through biological fermentation processes using renewable feedstocks. The list of organic compounds that can be derived from renewable feedstocks includes α,ω-diacids (succinic, fumaric, malic, glucaric, malonic, and maleic), 2,5-furan dicarboxylic acid, propionic acid, 3-hydroxy propionic acid, aspartic acid, glucaric acid, glutamic acid, itaconic acid, levulinic acid, 3-hydroxybutyrolactone, glycerol, and butanediols such as 1,4 butanediol (US Patent Application 20090047719), 1,3-butanediol (US Patent Application 20090253192), and 2,3-butanediol. Many other types of organic compounds, including, but not limited to, amino acids, vitamins, alcohols (such as ethanol, n-propanol, isopropanol, n-butanol, isobutanol, and higher alcohols), fatty acids, esters of fatty acids, hydrocarbons, isoprenoids, turpenes, carotenoids, amines, can also be produced using renewable feedstocks. Any such compound shall be referred to herein as a "desired compound". Although fermentation processes for many of these desired compounds have been developed, in order to compete with petrochemical processes, there is a constant need to improve the overall economics of fermentation, for example to improve product titer (final concentration in grams per liter of product) and product yield (grams of product per gram of carbon source such as glucose), and to reduce the titer of unwanted byproducts, such as acetate.

Many bacteria, including *Escherichia coli*, use a system for actively transporting glucose and other sugars into the cell called a phosphotransferase system (PTS). This system uses PEP (phosphoenol pyruvate) as the source of energy and phosphate for simultaneously transporting and phophorylating the sugar. PTS systems usually require four or more proteins that together function to import and phosphorylate the incoming sugar. Some of these proteins are common to all of the sugars that a given organism imports by a PTS, while other protein components of the PTS are specific for one or more particular sugars.

For example, in *E. coli*, the proteins that are common to all PTS pathways are PtsH and PtsI, encoded by the genes ptsH and ptsI, respectively. In addition to these two "common" PTS proteins, one or more additional sugar-specific PTS proteins are required to import and phosphorylate particular sugars. For example, import of glucose by the PTS requires two additional proteins named Crr and PtsG. Crr is a cytoplasmic protein with a single domain called A, and PtsG is a membrane protein with two domains named B and C. The phosphate group from PEP is relayed from protein to protein and is finally transferred to glucose as it is imported, at the 6 position to give glucose-6-phosphate inside the cell. The order of the relay starting with PEP is PtsI, PtsH, Crr, and finally PtsG. Historically, these proteins have also been called by other names, such as EI, HPr, EIIA$^{Glc}$, and EIIBC, respectively. As another example from *E. coli*, fructose is imported by a similar relay using PtsI, PtsH, FruA, and FruB, the last two of which are also known as EII$^{Fru}$ and EII$^{Fru}$, respectively. For some sugars, for example mannitol, the sugar-specific protein domains corresponding to A, B, and C as mentioned above for glucose are fused into one membrane bound polypeptide, while for other sugars, for example mannose, the A and B domains are fused into one cytoplasmic polypeptide, while the membrane bound component is comprised of two subunits called C and D.

In all cases, the system relies on the "common subunits" (PtsI and PtsH in *E. coli*), and PEP is the source of energy and phosphate. As a result, every molecule of sugar imported by a PTS system results in the utilization of one molecule of PEP and the production of one molecule of phosphorylated sugar and one molecule of pyruvate. However, PEP is also an obligate intermediate in several biochemical pathways, such as 1) formation of pyruvate and ATP by pyruvate kinase, 2) the anapleurotic pathways catalyzed by PEP carboxykinase and PEP carboxylase, which both feed carbon into the TCA (tricarboxylic acid) cycle, and 3) the entry into the common aromatic amino acid and aromatic vitamin biosynthetic pathway catalyzed by one or more isozymes of 3-deoxy-D-arabinoheptulosonate-7-phosphate synthase (DAHP synthase). Thus there is an inevitable competition for PEP between the PTS system for sugar import and the other pathways just mentioned.

Since many bacteria, including both Gram positives and Gram negatives, use a PTS system, it is obviously a system that has prevailed under many circumstances throughout evolution. However, under anaerobic conditions, production of ATP from sugars such as glucose is much less efficient than under aerobic conditions, and the so-called "substrate level" phosphorylation, for example, by pyruvate kinase, becomes a larger portion of the ATP production budget than under aerobic conditions where oxidative phosphorylation provides the majority of the ATP budget. As such, it is noteworthy that some organisms, such as *Saccharomyces cerevisiae* and *Zymomonas mobilis*, both of which are well adapted to anaerobic growth on glucose and other sugars, do not have a PTS system, but instead use a facilitated diffusion protein (also called a permease) to import glucose and other sugars. Furthermore, when organisms that natively use a PTS are genetically engineered to overproduce particular compounds by fermentation, the pathways in many cases use PEP as an intermediate, so that the PTS competes with the desired biosynthetic pathway for PEP. Alleviation from this competition by reducing the activity of the PTS is known to increase flux to a desired biosynthetic pathway.

For example, PEP is an intermediate in the reductive branch of the tricarboxylic acid (TCA) cycle that leads to succinate. During the metabolic evolution of KJ122, an *E.*

*coli* succinate producer, a frameshift mutation arose in the ptsI gene, which resulted in an increase in succinate production from glucose. Reinstalling a wild type ptsI gene caused a drastic reduction in succinate production, proving that the ptsI mutation contributed strongly to the strain improvement.

For another example, aromatic amino acids are built from PEP and erythrose-4-phosphate. Deletion of three pts genes (ΔptsHI, crr) in an *E. coli* strain was shown to increase flux to the aromatic amino acid biosynthetic pathway when cells are grown on glucose as the carbon source.

In both of the above examples, import of glucose is presumably still accomplished at some level by the so-called galactose permease (GalP, encoded by the galP gene). In the first example, a mutation that reduced the activity of a repressor (Gals) of the galP gene was found to result from metabolic evolution (WO2011/123154). In the second example, one or more mutations occurred after deletion of pts genes that resulted in an increase in growth rate. The resulting strain depended on galP for significant growth on glucose, and one or more mutations in the strain could have been related to an increase in expression of galP (U.S. Pat. No. 6,962,794). However, the strains from this second example produced only low titers of aromatic amino acids after engineering the "Pts−/Glu+" strains for aromatic amino acid production. Phenylalanine, tyrosine, and tryptophan were produced at 1.7, 0.8, and 2.2 g/l respectively. Since these titers are nowhere near high enough to support an economically attractive commercial process, it is not clear that the invention disclosed in U.S. Pat. No. 6,962,794 is useful for commercial production. As such, there is still a need to improve fermentation parameters for economically viable commercial production of chemicals by fermentation.

Although the use of GalP for glucose import conserves PEP, it is a proton symporter, so it consumes about ⅓ of an ATP for each glucose molecule transported. Some microorganisms, for example the bacterium *Zymomonas mobilis* and the yeast *Saccharomyces cerevisiae* use facilitated diffusion for importing glucose. *Z. mobilis* has one facilitator protein that functions to import both glucose and fructose. *S. cerevisiae* has at least 14 different hexose importers, many of which import glucose and at least some of which import fructose as well. This mode for glucose import requires no ATP expenditure until the sugar is inside the cytoplasm, after which an ATP is consumed to form glucose-6-phosphate to allow the sugar to enter glycolysis. Most importantly, unlike for the PTS system, no PEP is consumed. As such, facilitated diffusion clearly works well for some organisms, and costs the cell less in terms of PEP and ATP than either a PTS system or a proton symporter such as GalP. Ingram et al. (U.S. Pat. No. 5,602,030) demonstrated that the facilitated diffusion protein (Glf, encoded by the glf gene) from *Zymomonas mobilis*, together with a glucokinase (Glk, encoded by the glk gene), also from *Zymomonas mobilis*, expressed from those genes on a multicopy plasmid, could functionally replace the PTS to support growth in a minimal glucose medium of an *E. coli* strain, where the parent had no native glucose facilitated diffusion capability, and other glucose import systems had been disabled by mutation. The recombinant *E. coli* ptsG−, ptsM−, glk− strain ZSC113 containing the two *Z. mobilis* genes glf and glk on a plasmid could grow aerobically on minimal glucose medium.

These disclosures proved that the *Z. mobilis* proteins could function in *E. coli* enough to support growth aerobically with a specific growth rate of 0.53 hr-1. However, wild type *E. coli* using the native PTS for glucose import has an aerobic specific growth rate of 1.0 to 1.2 hr-1), so the strains engineered in U.S. Pat. No. 5,602,030 to use glf appear to be severely limited by glucose uptake. Moreover, the disclosures did not show that the facilitated diffusion system could support anaerobic growth. A number of important chemicals produced by fermentation require robust anaerobic growth to support an economically attractive commercial production system (WO2012/018699). The examples in U.S. Pat. No. 5,602,030 and Snoep et al (1994) showed that modest growth could be obtained by expressing glf and glk from a multicopy plasmid, but it was not demonstrated that growth could be supported by integrated copies of the glf and glk genes, yet it is often desirable for commercial scale production to use strains that do not contain a plasmid. Finally, U.S. Pat. No. 5,602,030 did not demonstrate that a glf-based system could support high titer production of a commodity chemical such as ethanol or succinate in *E. coli* or any other organism that does not natively use facilitated diffusion. As such, it was not clear from the disclosure of U.S. Pat. No. 5,602,030 alone that a glf could replace the PTS and result in an economically attractive fermentation processes for producing a desired chemical in a host strain that does not have a native facilitated diffusion system.

Tang et al (2013) went a couple steps further to show that anaerobic production of succinate could be achieved by expression of *Z. mobilis* glf in combination with a glucokinase in an *E. coli* strain background that was ΔptsI, ΔldhA, ΔpflB, pck*. However, the best succinate production in this system was modest, only 220 mM (26 g/l) in 96 hours. Despite having optimized by combinatorial modulation the expression of glf and glk, this titer and productivity is nowhere near that of previously published strains that produced 83 g/l succinate without the use of glf. Thus, despite the more advanced work of Tang et al., it had still not been demonstrated that the use of facilitated diffusion for glucose import was useful for actually improving fermentation production parameters at levels that would be necessary for economically attractive commercial production, which would be at the benchmark of at least 83 g/l (WO2012/018699). To further complicate the potential replacement of a PTS by glf, in *E. coli*, and presumably in other bacteria, the components of the PTS have many diverse regulatory functions that affect many different metabolic pathways, so it is impossible to predict what the effects will be of a deletion in any one or more of the PTS genes on the overall physiology and fermentative properties of any resulting modified strain. Native *Z. mobilis* strains, which naturally use facilitated diffusion for glucose uptake, are capable of producing up to about 60 g/l ethanol and a similar quantity of carbon dioxide from glucose. An engineered strain of *Z. mobilis* is reported to produce 64 g/l succinate from glucose (EP20070715351). However, this fermentation required 10 g/1 of yeast extract in the fermentation medium, which is undesirable for commercial production of succinic acid, both because of its expense and the increased cost required for downstream purification of the succinate from the yeast extract components. Furthermore, *Z. mobilis* is often not a convenient or optimal host organism for use in fermentative processes.

Thus, to summarize the prior art, it had been shown that *E. coli* can be engineered to use facilitated diffusion of glucose to support aerobic growth to a modest rate, and to support a modest level of succinate production anaerobically, but there has been no disclosure of any bacterial strain or process that has been engineered to confer the non-native use of facilitated diffusion for glucose import and that is improved over strains using native glucose import systems such as PTS and/or GalP for production of a chemical by fermentation. Furthermore, there has been no disclosure of any bacterial strain or process that uses facilitated diffusion for glucose import and that is capable of producing succinate or any chemical other than ethanol and carbon dioxide at a titer, yield, and rate that is high enough in a medium that would be commercially attractive, such as a minimal glucose medium. As such, there is still a need for improved strains that can produce succinate and chemicals in a process that is economically attractive when all factors including productivity, cost of the medium, and downstream purification are taken into account.

SUMMARY OF THE INVENTION

This present invention provides biocatalysts (for example genetically engineered microorganisms) and methods for using facilitated diffusion of glucose for improving the fermentative production of commercially important products, for example, but not limited to, specialty and commodity chemicals. Specifically, the present invention is useful in the fermentative production of organic acids, amino acids, and other biochemicals that have PEP as a biochemical intermediate in their biosynthetic pathway, using sugar-containing renewable feedstocks. As a specific example, the present invention is useful in the fermentative production of succinic acid from a glucose, fructose, or sucrose-containing renewable feedstock using biocatalysts that have been constructed to use facilitated diffusion of a sugar. The principles of the present invention can be applied to many other desired chemical compounds that can be produced by fermentation, particularly chemicals intermediates of the TCA cycle or derivatives thereof, such as fumaric acid, malic acid, glutamate, derivatives of glutamate, aspartate, derivatives of aspartate, aromatic amino acids (phenylalanine, tyrosine, tryptophan), and compounds derived from intermediates in the central aromatic pathway, such as vitamins and cis, cis-muconic acid.

According to the present invention, genes coding for the proteins involved in facilitated diffusion of sugars such as glucose can be introduced into a wide variety of biocatalysts either to confer a new ability to the biocatalyst to import a sugar as a source of carbon and energy from the fermentation medium by facilitated diffusion, or to augment or improve an already existing capacity of the biocatalysts for sugar transport and metabolism. Strains engineered to have the added ability to import sugars by facilitated diffusion can have improved fermentation parameters when compared to parameters of the parent strain, such as increased titer (g/l of desired chemical product), increased yield (grams of product produced per gram of sugar consumed), increased specific productivity (g/l-hr of product formation), and/or decreased titer of unwanted byproducts such as acetate, pyruvate and/or amino acids. These improved parameters can result from conservation of energy (for example use of less ATP for formation of proton gradients to drive proton symporters such as GalP), conservation of PEP for pathways that use PEP as an intermediate, such as the succinate pathway(s), and decreasing of overflow metabolism into acetate production pathways or other unwanted pathways.

This approach is particularly advantageous for production of chemicals that are derived at least in part from or through PEP, such as succinate, malate, fumarate, lactate, ethanol, butanols, propane diols, 3-hydroxypropionic acid, acrylic acid, propionic acid, lactic acid, amino acids such as glutamate, aspartate, methionine, lysine, threonine, and isoleucine, compounds derived from the central aromatic pathway such as phenylalanine, tyrosine, tryptophan, aromatic vitamins, aromatic vitamin-like compounds, and any other compound that is derived from PEP as a biosynthetic intermediate.

In one embodiment, the present invention provides biocatalysts that do not natively have the ability to import a sugar by facilitated diffusion with an added heterologous gene (or genes) that confers a new ability to import a sugar by facilitated diffusion. In another embodiment, the present invention provides novel biocatalysts that produce a higher titer of a desired fermentation product than the parent biocatalyst. In another embodiment, the present invention provides novel biocatalysts that produce a higher yield of a desired fermentation product than the parent biocatalyst. In another embodiment, the present invention provides novel biocatalysts that produce a higher specific productivity for a desired fermentation product than the parent biocatalyst. In another embodiment, the present invention provides a novel biocatalyst that produces a lower titer of an undesired desired byproduct than the parent biocatalyst.

The gene or genes that code for the protein or proteins that function in the facilitated diffusion of a sugar can be derived from any organism that has the native ability to carry out facilitated diffusion of a sugar, the only requirement being that the protein or proteins are able to function in the new host. The gene encoding a sugar kinase, for example a glucokinase, that is required to phosphorylate the sugar after it enters the cytoplasm can be derived from the same donor from which came the gene(s) for facilitated diffusion, or a native sugar kinase gene from the recipient host can be used, or a combination of both sugar kinases can be used.

In another embodiment, the present invention provides for methods for producing a desired fermentation product comprising cultivating a genetically engineered microorganism that used facilitated diffusion to import a sugar.

In another embodiment, the present invention provides for methods for improving fermentation performance parameters (titer, yield, specific productivity, minimizing byproduct formation) of strains engineered to use facilitated diffusion.

In another embodiment, the present invention provides for methods for achieving an improved balance of facilitated diffusion and sugar kinase activity leading to improved growth and fermentation parameters in genetically engineered microorganism that used facilitated diffusion to import a sugar.

According to the present invention, one approach is to genetically transfer a facilitated diffusion system for importing a sugar from a second donor organism that naturally contains the relevant genes (for example glf or glk or a combination thereof) into a first recipient organism that does not naturally contain said relevant genes, so as to confer on said first recipient organism a new ability to import said sugar by facilitated diffusion. In a preferred embodiment, the first recipient has been previously engineered or constructed to be devoid of, or substantially reduced in, its ability to import said sugar by any native system or systems present in a parent or ancestor of said first recipient strain. In such an embodiment, the resulting strain is in effect forced to use facilitated diffusion for growth on said sugar.

In a preferred embodiment, the first recipient strain is an *E. coli* strain, and the second donor strain is *Zymomonas mobilis* CP4. In a more preferred embodiment, said first strain is WG53, which in turn is derived from KJ122 by deletion of ptsH, ptsI, and galP. The exact nature of the deletions of ptsH, ptsI, and galP can vary widely, the only important criterion being that the activities of the PtsH, PtsI, and GalP proteins are eliminated or substantially reduced.

The first recipient organism of the invention can vary widely, the only criterion being that it does not natively contain a protein that functions in facilitated diffusion for a sugar such as glucose. In addition to *E. coli*, examples of first recipient organisms include, but are not limited to: *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter parqffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutanzicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia* chrysantherni, *Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia inarcescens, Salmonella typhimurium, Salmonella schottmulleri, Bacillus subtilis, Bacillus licheniformis, Bacillus amylolliquefaciens, Klebsiella oxytoca, Klebsiella pneumoniae, Acinetobacter baylyi, Corynebacterium glutamicum Brevibacteium flavum, Mannhemia succiniproducens* and *Anaerobiospirilum succiniproducens,* and *Xanthomonas citri.*

Examples of second donor organisms are any strain or species that has a native facilitated diffusion system for a sugar, for example *Zymononas mobilis* strains (in addition to strain CP4), *Homo sapiens, Azospirillum amazonense,* Flavobacteriaceae bacterium S85, *Saccharomyces cerevisiae* or other yeast genera.

In another embodiment, a first parent strain is first constructed to use facilitated diffusion for importing a sugar, and then the resulting stain is further engineered to overproduce a chemical of commercial interest such as succinic acid.

Novel aspects of this invention are that the glf gene from a non-pathogenic, robust sugar utilizer has been stably integrated into the chromosome of a bacterium, such that the newly constructed bacterium can produce a commercially viable product with an economically viable process. The titer, yield and/or specific productivity of product from glucose or another sugar is greater than those parameters of the parent organism. The glf gene is integrated at a site in the chromosome that does not interfere with any relevant aspect of growth or product production. The acetate titer is less than that of the parent strain at about 45 to 48 hours in a representative fermentation, allowing a 2 day fermentation cycle time, unlike a prior art example. Strains in the prior art that used facilitated diffusion for sugar import did not produce sufficient titers of the desired product to be economically attractive. Another novel aspect of this invention is that by using facilitated diffusion for sugar import, it was unexpectedly found that the production of the unwanted byproduct acetate or acetic acid was significantly reduced. The prior art strain KJ122 produces about 5 to 7 g/l acetate in a typical fed glucose fermentation (WO2012/018699), while new strains of the invention produce only about 4.2 g/l or less.

Additional advantages of this invention will become readily apparent from the ensuing description.

Figure 1:
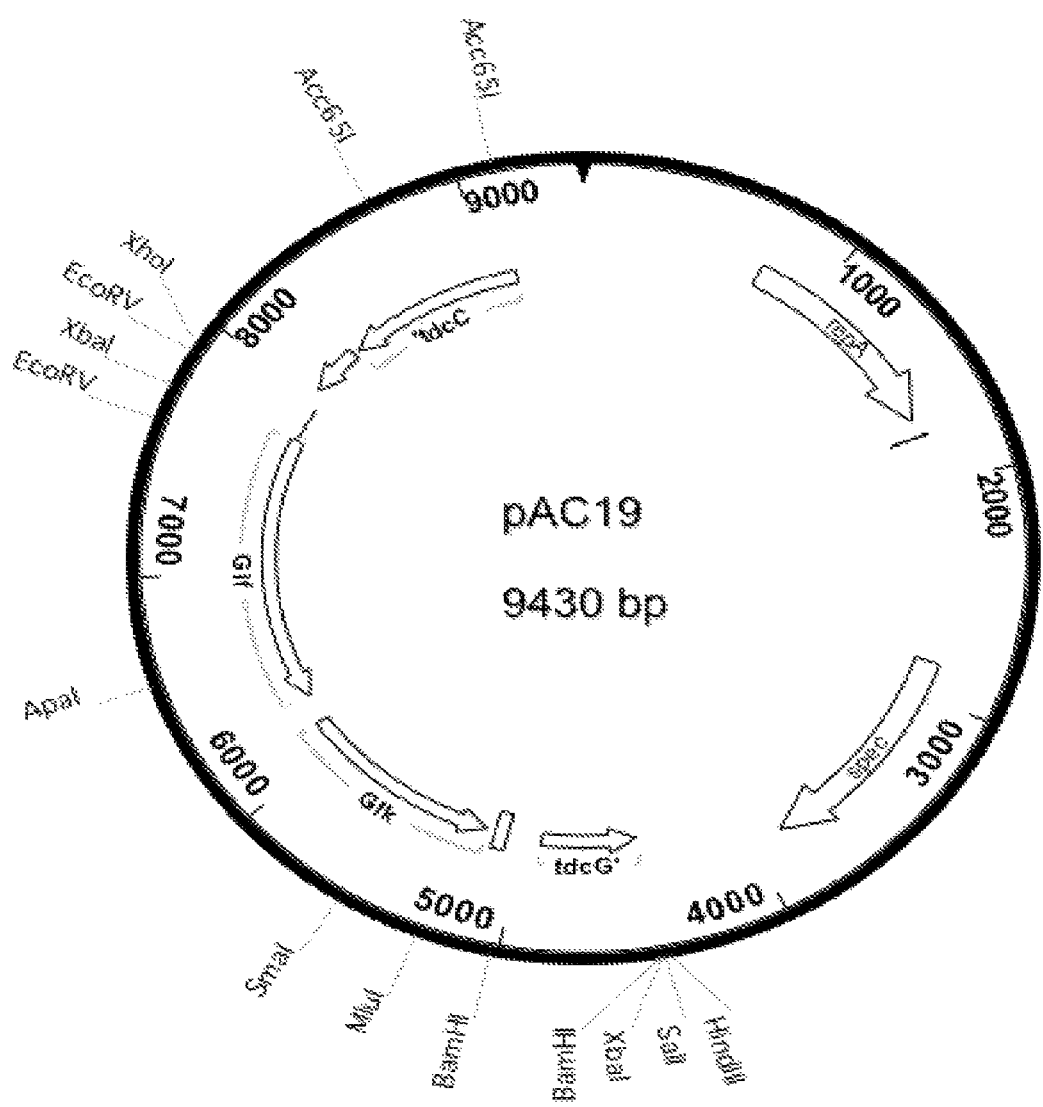
FIG. 1 Structure of plasmid pAC19, a source of an expression cassette for *Z. mobilis* glf and glk.
Figure 2:
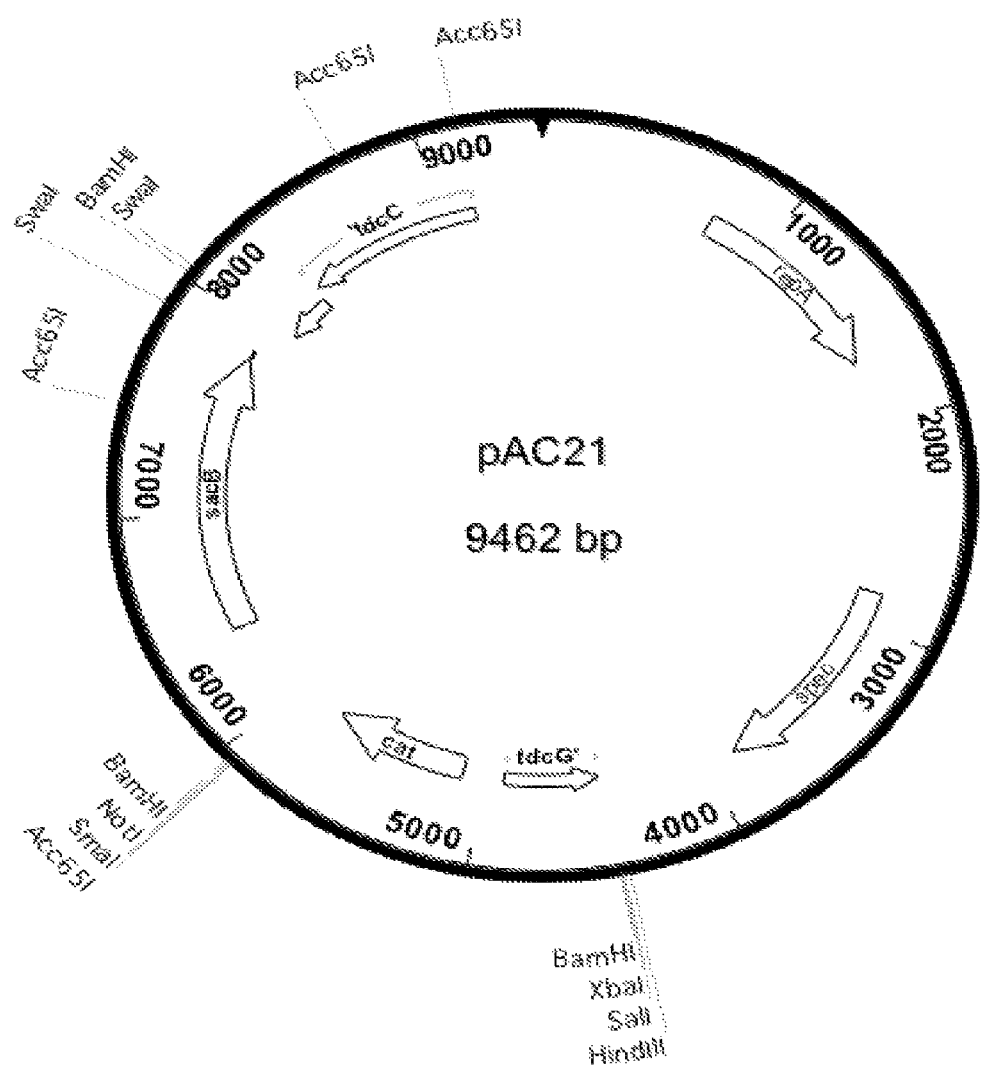
FIG. 2 Structure of plasmid pAC21, a source of a selectable and counter-selectable cassette containing cat (chloramphenicol resistance) and sacB (levan sucrase) genes.
Figure 3:
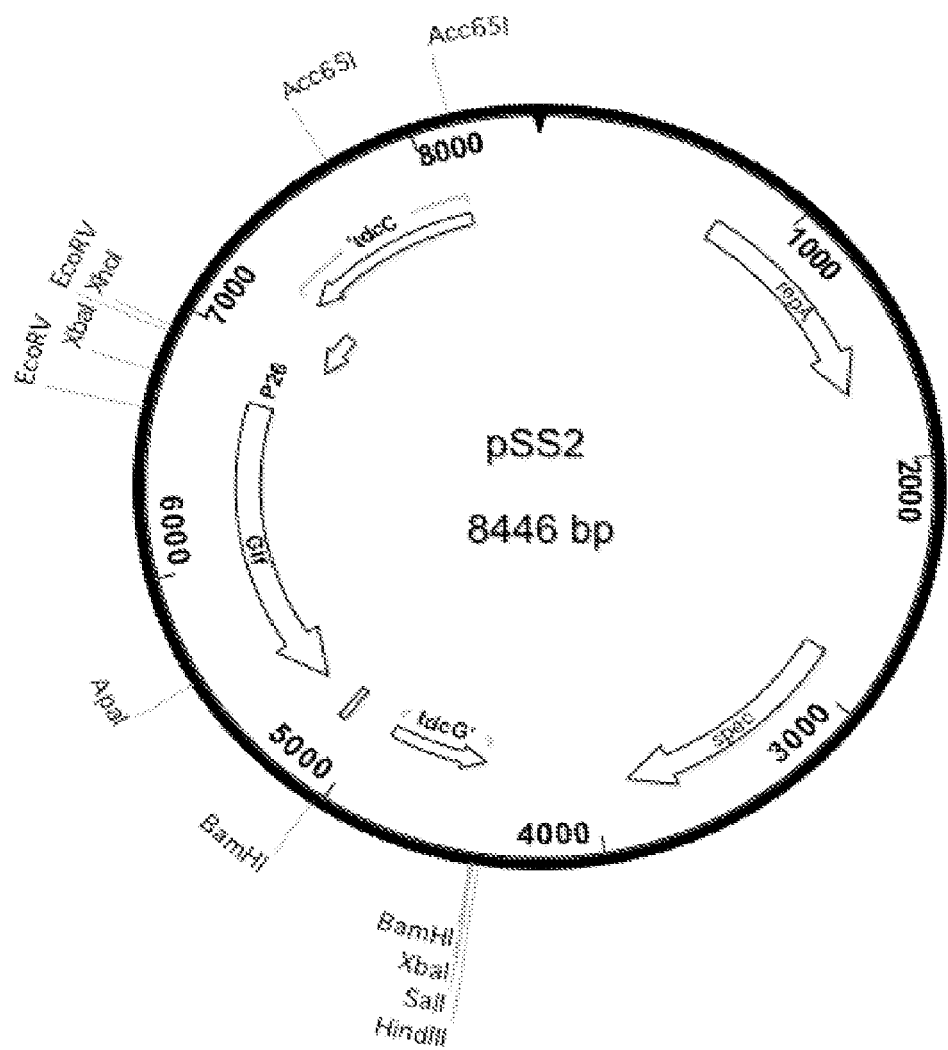
FIG. 3 Structure of plasmid pSS2, a source of an expression cassette for *Z. mobilis* glf without glk.
Figure 4:
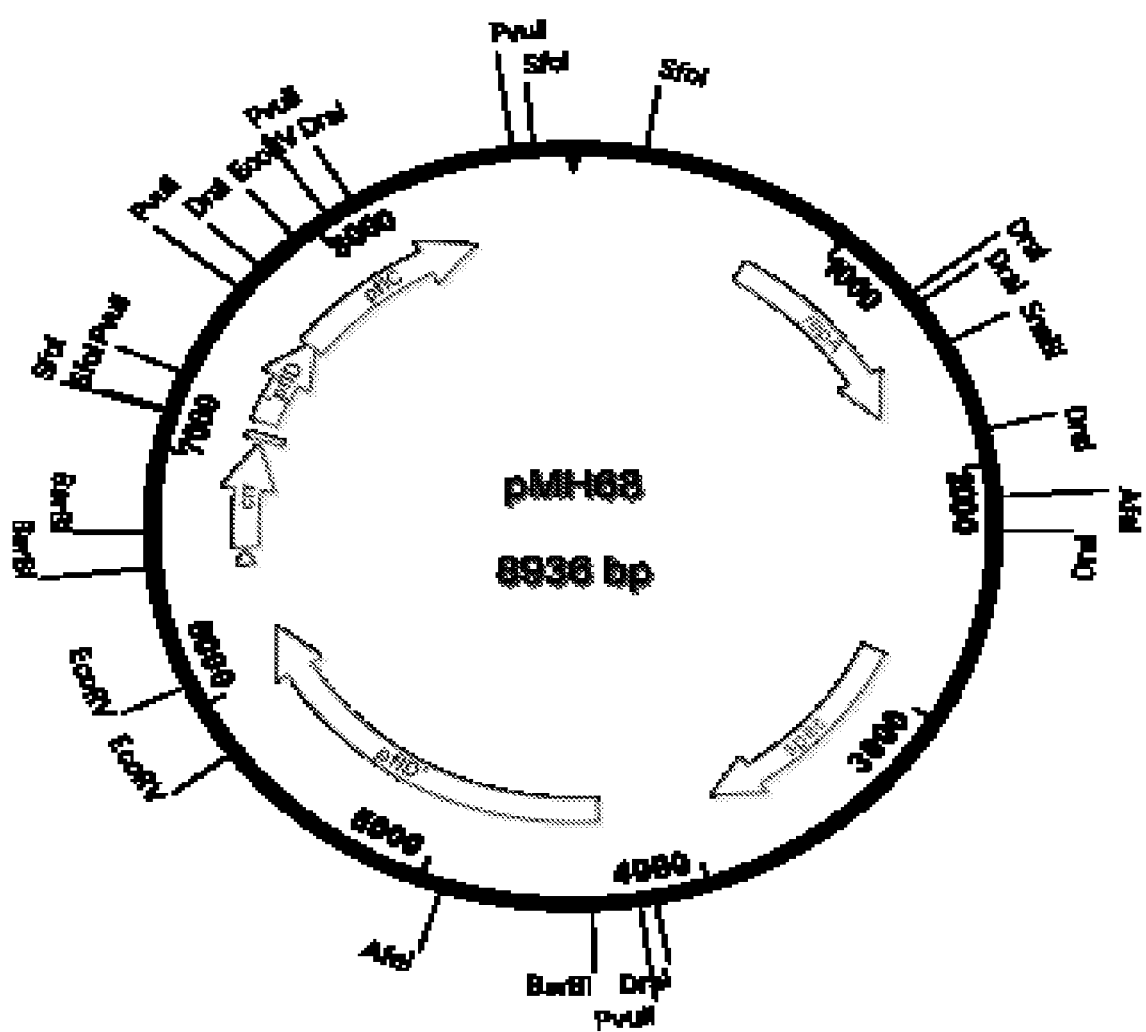
FIG. 4 Structure of plasmid pMH68, a source of an expression cassette for integration of a second copy of the *E. coli* crr gene at the pflD locus.

Table 1. Production of succinate by AC15 in 7 liter fermentors.

Table 2. Production of succinate by red mutants of AC15 in 500 ml microaerobic fermentors.

Table 3. Production of succinate by two isolates of SS8 in 500 ml microaerobic fermentors.

Table 4. Production of succinate by YSS41 in 20 liter microaerobic fermentors.

Table 5. Production of succinate by MH141 in 500 ml microaerobic fermentors.

Table 6. Succinate production by *E. coli* strains KJ122 and YSS41 in 20 liter fermentors under optimized aeration conditions for both strains.

DETAILED DESCRIPTION OF THE PREFERRED EMBODIMENTS

Definitions

When the phrase "for example" or "such as" is used, the subsequently mentioned items are meant to be illustrative examples for the idea or concept being disclosed. The subsequently mentioned items are not meant to be limited to the examples given, since any other specific item or example that would fall under the generalization of the idea or concept is meant to be included. For any given compound, it might be more appropriate to produce a salt of said compound, so for example, succinic acid might be produced at pH near 7 as a salt of sodium, potassium, calcium, magnesium, ammonium, etc., while lysine might be produced as a salt of chloride, sulfate, bicarbonate, etc. As such, any time a compound is named herein, any salt of said compound is meant to be included, and any time a salt is named, the free acid or free base is also meant to be included. Thus, for example, "succinate" is meant to include "succinic acid" and vice versa, and "acetate" is meant to include "acetic acid" and vice versa.

"Facilitated diffusion" means the action of a system, typically comprising an integral membrane protein situated in a biological membrane (for example the inner membrane of a Gram negative bacterium or the single membrane of a Gram positive bacterium), or a complex of more than one protein molecules situated in a biological membrane, that functions to specifically allow one or more chemicals called the "substrate" (for example glucose and/or fructose), but not chemicals in general (for example water and cytoplasmic metabolites other than the specific substrate), to cross through the membrane without any energy (such as that provided by hydrolysis of ATP or PEP) or gradient of a different chemical (for example a proton gradient) provided directly to the system by the cell. If there is a concentration gradient, for example if the concentration of a substrate is higher outside the cell than inside the cell, there will be a net flux of that substrate into the cell at a rate that is faster than would occur if the facilitated diffusion system were absent. The protein(s) that function for facilitated diffusion typically have a binding affinity that is specific for one or more substrates and allows the system to assist passing the substrate across the membrane at relatively low concentrations of several millimolar or less. Some types of facilitated diffusion can function by creating a pore or channel through the membrane that discriminates in favor of a substrate, and in other types the protein(s) can bind the substrate on one side of the membrane and then rotate through the membrane to release the substrate on the opposite side of the membrane. A facilitated diffusion protein (sometimes called simply a facilitator) is a protein component of such a system. Thus, the thermodynamic driving force for facilitated diffusion is a gradient of substrate concentration, in which the substrate (for example a sugar) flows from a higher concentration outside of a cell to a lower concentration inside the cell. We shall use the genetic symbols Glf and glf to respectively mean a facilitated diffusion protein and a gene encoding such a protein that has specificity for glucose. We usually consider Glf to be a comprised of a single polypeptide chain, but a Glf could be a complex comprised of more than one polypeptide chain. Although the specific examples of Glf written herein are bacterial in origin, our definition is meant to include facilitated diffusion system derived from any organism. For example, it is well known that the yeast *Saccharomyces cerevisiae* and other yeasts have one or more facilitated diffusion proteins for importing hexoses (for example glucose and fructose) named HXT1, HXT2, HTX3, HTX4, HTX5, HTX6, HTX7, etc.), and human erythrocytes use facilitated diffusion to import and export glucose via a protein named GLUT1. The mechanism of action of Glf's can vary widely, including pore-facilitated transport and carrier-facilitated transport. Although the specific examples given in this specification disclose a Glf that has good specificity for glucose, it is known in the art that a Glf protein can be active on more than one sugar, for example Glf from *Zymomonas mobilis* and *Saccharomyces cerevisiae* can be active on fructose as well as glucose.

Proton symport is defined as a system for importing a substrate across a biological membrane that uses a proton gradient as a driving force. A higher concentration of protons outside of the cell has a thermodynamic tendency to diffuse back into the cell. This thermodynamic pressure is used to carry in a substrate such as a sugar. A proton symporter is a protein or complex of proteins that functions to provide proton symport. An example of a proton symporter is the GalP protein of *E. coli*, which is well known to function in the import of galactose, glucose, and other sugars.

A glucokinase and a fructokinase are enzymes that catalyze phosphorylation of glucose, fructose, or other sugar, usually at the $6^{th}$ carbon position, but alternatively possibly at the $1^{st}$ carbon or another position. We shall use the genetic symbols Glk and glk to respectively mean a glucokinase and a gene that encodes a glucokinase. Frk and frk mean a fructokinase and a gene that encodes a fructokinase, respectively.

A crr gene is a gene that encodes an $EIIA^{glc}$ component of a PTS, such as the crr gene of an *E. coli* strain or of a *Bacillus subtilis* strain or a homolog of such a crr gene.

A PTS (phosphotransferase system) is a group of proteins that act together to pump a sugar into a cytoplasm and simultaneously phosphorylate the sugar, using PEP as the source of phosphate and energy. Examples of genes encoding PTS proteins from *E. coli* include ptsH, ptsI, crr, ptsG, fruA, fruB, manX, manY, and manZ. The corresponding proteins are named PtsH, PtsI, Crr, PtsG, FruA, FruB, ManX, ManY, and ManZ. However, there are many more examples from *E. coli* and other prokaryotes, and these proteins can have alternate names, for example Crr is sometimes named $EIIA^{glc}$. Some of the PTS proteins are more specific to one or more particular sugars than to other sugars, while some PTS proteins, for example PtsH and PtsI from *E. coli*, are used in common for many different sugars.

In this specification, the term "microaerobic" means that the feed rate of air is less than 0.1 volume of air per volume of liquid culture per minute. In 7 and 20 liter fermentor examples disclosed herein, this is accomplished with a sparger and flow meter, or by allowing the tank to breathe through a sterile membrane attached to the top of the tank without any forced air flow. In 500 ml fermentor tank examples disclosed herein, no air is deliberately introduced, but a small amount of air is introduced from leakage, feeding of the base solution, and taking of samples.

A "minimal medium" is a microbial growth medium comprised of water, a pure carbon source (such as a substantially pure sugar or mixture of substantially pure sugars), mineral salts (for example potassium, sodium, magnesium, calcium, bicarbonate plus carbonate, phosphate, sulfate and chloride), a pure nitrogen source such as ammonium or urea, trace metals (iron, copper, zinc, manganese, cobalt, molybdenum, and optionally borate), optionally glycine betaine (also known as simply betaine), and optionally an antifoam agent. Minimal media do not contain any complex (also known as "rich") nutrient source such as yeast extract, corn steep liquor, soy hydrolysate, broth, casein hydrolysate, grain, legume, or any other "undefined" mixture of nutrients that typically would be derived from an agricultural source without any physical or chemical purification or separation steps. Reasonably pure sugars derived from sugar cane, corn starch, sorghum starch, tapioca starch, or any other reasonably pure starch source is considered to be acceptable for a minimal medium. A minimal medium can contain one or a few pure chemicals to satisfy a particular growth requirement (auxotrophy or bradytrophy) or to enhance a biochemical pathway. For example, some strains require a vitamin such as biotin, which can be added at small concentrations without a significant negative impact on a process. As another example, addition of a vitamin such as thiamine, while not absolutely required for growth, can nonetheless enhance growth or a biochemical pathway. Minimal media are preferable for fermentative production of many chemicals due to the relatively low cost of the components, and due producing cleaner fermentations broths that allows for more favorable economics for downstream purification of the desired chemical. Ethanol production is an exception, since downstream purification can be accomplished with distillation, an economically attractive method for purification of the desired product even from complex media.

An aromatic biochemical means any one or more of the following: phenylalanine, tyrosine, or tryptophan, or any derivative thereof (such as L-dihyroxyphenylalanine, melatonin, indole, indole acetic acid, indigo, serotonin, cinnamic acid, hydroxy styrene), a vitamin or vitamin-like compound containing an aromatic moiety (such as p-hydroxybenzoic acid, 2,3-dihydroxybenzoic acid, p-amino benzoic acid, folate, tocopherol, pyrroloquinoline quinone).

A homolog of a first gene or protein is defined as a second gene or protein in which the second protein or the protein inferred to be translated from the second gene has the same or a similar biochemical function as the first protein or protein inferred to be translated from the first gene, and in which an alignment of the first and second proteins or first and second inferred translated proteins results in a 25% or greater identity or similarity for a region of at least 50 amino acids in length, when using the default parameters of a publically available computer alignment program such as BLAST.

A mutation is any change in a DNA sequence relative to the DNA sequence of the related wild type or native gene. A mutation can be a single or multiple base change that introduces a premature stop codon or an amino acid that is different from the wild type amino acid at that position. A mutation can be an insertion or deletion of one or more bases that creates a frame shift that results in a protein that is significantly different from the wild type protein. A mutation can be a deletion that removes much, most, or all of a coding region (also known as an open reading frame or orf). One type of mutation removes one or more entire orfs plus additional non-coding DNA either upstream or downstream from the coding region, or both. A mutation can result from insertion of a relatively large DNA sequence (more than about 100 bases), for example an insertion element (for example IS186 or IS4) or a transposon (for example Tn10). When the intent is to remove a function, a preferable mutation is a deletion of all or most of an orf however, smaller mutations such as single base changes or insertions can often accomplish removal of a function for all practical purposes. Mutations can be spontaneous, induced by mutagenesis, or constructed by genetic engineering. Some mutations, when desired to accomplish a strain improvement, are mutations that decrease or eliminate a biological function, such as particular elements of a PTS. However, some mutations, when desired to accomplish a strain improvement, are mutations that increase a biological function, for example a "promoter up mutation" can increase the expression of a desired gene, such as a glf gene.

"Exogenous" means a gene or protein derived from a second genus that has been installed in a first genus, where said second genus is a different genus from said first genus.

A gene is defined as a region of a chromosome that encodes a protein or enzyme, and is meant to include both the open reading frame that corresponds to the protein or enzyme and any DNA sequences surrounding the open reading frame that contribute to controlling the level or rate of production of the protein or enzyme, such as promoters, ribosome binding sites, operators, regulatory protein binding sites, DNA corresponding to 5' untranslated mRNA leader sequences, terminators, and antiterminator sites. When two or more open reading frames that correspond to protein coding DNA sequences are under the control of a single promoter and a single terminator, the whole region encompassing the promoter, open reading frames corresponding to protein coding DNA sequences and the terminator is referred as an operon. For example, when the exogenous genes glf and glk are under the control of a single promoter and a single terminator, it is referred as glf-glk operon.

The present invention provides biocatalysts for succinic acid production in high titer, yield and productivity using a minimal medium with a sugar as a carbon source. The term "yield" as defined in this invention refers to the number of grams of product (such as succinic acid) produced per gram of sugar (such as glucose or sucrose) consumed. The term "productivity" as defined in this present invention refers to the number of grams of product (such as succinic acid) produced per liter of culture per hour. The term "titer" is defined as the concentration of product (such as succinic acid) in the fermentation broth in grams per liter. The desirable yield for succinic acid is in the range of 0.8-1.2 grams of succinic acid produced per gram of sugar consumed. The desirable productivity for succinic acid in this present invention is in the range of 1 gram or more of succinic acid produced per liter per hour. The desirable titer of succinic acid is greater than 26 g/l, or more preferably greater than 64 g/l, and most preferably greater than 83 g/l in a fermentation time of 48 hours or less.

The bacterial growth rate is measured in terms of the rate of increase in the optical density at 550 or 600 nanometers of a liquid culture resulting from the bacterial multiplication. The bacterial growth rate is also expressed in terms of time required for doubling of bacterial cells. In the bacterial cells suitable for the present invention, the bacterial cells are expected to have a doubling time of between 20 minutes and 3 hours.

According to the present invention, the biocatalyst for succinic acid production can be developed in two different ways. Under the first approach, a wild type bacterial species is genetically manipulated and, optionally, evolved, to grow efficiently using facilitated diffusion for import of glucose or other sugar. Once such a strain is constructed, subsequent genetic manipulations are carried out in the metabolic pathways to obtain a bacterial strain that produces succinic acid or another desired chemical with high titer, yield and productivity, for example, by following methods known in the art.

The patent applications published under Patent Cooperation Treaty with the publication No. WO 2010/115067 and United States Patent Application Publication No. US 20100184171 provide the details about the genetic engineering techniques useful in generating a strain of *E. coli* with improved succinic acid production capacity. These two patent applications are incorporated herein by reference.

Under the second approach, a bacterial strain already developed to have a commercially attractive yield and productivity for a chemical such as succinic acid as described in the patent application publications US 20100184171 and WO 2010/115067 is used as a parental strain. Further genetic manipulations, and optionally, evolution, are then carried out with this strain to obtain a bacterial strain that has the ability to use facilitated diffusion to import glucose or another sugar to produce succinic acid at a commercially attractive titer, yield, and productivity.

As a specific example, this present invention discloses biocatalysts and methods that have improved ability over that of the prior art to produce succinic acid at high enough titer, yield and productivity while gaining the new ability to import a sugar by facilitated diffusion. For example, the KJ122 strain of *E. coli* described by Jantama et al. can be selected as the starting strain for the present invention. The KJ122 strain of *E. coli* is reported to have the ability to produce succinic acid in a minimal medium at high titer and productivity.

The KJ122 strain of *E. coli* was derived from the *E. coli* C strain through gene deletions and metabolic evolution as described in US Patent Application Publication No. 20100184171 and in the International Patent Application Publication No. WO 2010/115067. These two patent application publication documents providing details about the genetic changes that led to the development of the KJ122 strain of *E. coli* are incorporated herein by reference. KJ122 does not have any substantial ability to import glucose as a source of carbon by facilitated diffusion in the production of succinic acid. The absence of this function in KJ122 is attributable to the lack of a gene that encodes a Glf protein. The inventors have discovered genetic approaches that enable KJ122 to more efficiently use glucose as a source of carbohydrate while retaining or improving its original ability to produce succinic acid at high titer, yield, and productivity in a minimal medium.

The term "carbohydrate" as used in this invention includes mono-saccharides such as glucose, fructose, xylose, and arabinose, disaccharides such as sucrose, melibiose, maltose and lactose, trisaccharides such as raffinose and maltotriose, and higher oligosaccharides, and hydrolysates derived from the enzymatic or chemical digestion of polysaccharides such as starch, cellulose, and biomass. Simple carbohydrates, those with from one to three saccharide units, are referred to herein as "sugars", for example glucose, fructose, sucrose, maltose, etc.

The terms "PTS organism" or "PTS bacterium" refers to a bacterium which has the capacity for a carbohydrate transport based on a PTS. The term "non-PTS organism," or "non-PTS bacterium" or "PTS$^-$" bacterium refers to bacterial cells that are mutated in one or more genes that encode a PTS function, such that the activity of the PTS is decreased relative to that of the wild tune PTS.

In one aspect, the present invention discloses the addition of genes to an organism in order to install or increase the activity of one or more proteins and/or enzymes involved in the import and conversion of a sugar into metabolic intermediates such as glucose 6-phosphate, glucose 1-phosphate, fructose 6-phosphate, or fructose 1-phosphate that can be further metabolized by the cell. The genes that encode relevant proteins or enzymes are chosen from a group consisting of a glf gene, an HXT gene, a glk gene, and a frk gene.

In another embodiment, the present invention provides a process for producing succinic acid or another chemical using facilitated diffusion to import a sugar such as glucose as a renewable feedstock. In one aspect, the present invention provides a process for producing succinic acid from a sugar-containing medium that makes use of a biocatalyst that has a decreased activity in at least one protein of the organism's native PTS system relative to that of the ancestral or parental strain. In another aspect, the present invention provides a process for producing succinic acid or other chemical in a sugar-containing medium that makes use of a biocatalyst that has a decreased activity in at least one protein of the organism's native sugar import system relative to that of the ancestral or parental strain involving use of a protein symport system, such as GalP.

The present invention provides ways to manipulate a PTS and in turn the bacterial carbohydrate uptake system. Since EI and HPr proteins function as "general" or "common" components of the PTS system, inactivation of either the ptsI gene coding for EI protein or the ptsH gene coding for HPr protein would lead to the complete inactivation of a PTS. There will be substantially less carbohydrate transport through the PTS system in bacterial cells where the activity of ptsH or ptsI or both has been decreased or eliminated. When the PTS is partially or completely inactivated, the bacterial cell has to depend on one or more other alternative permease systems for carbohydrate transport.

When there is active glucose transport through PTS, the EIIA$^{Glc}$ remains unphosphorylated as there is a carbohydrate substrate for accepting its phosphate group. However, when there is no glucose in the medium, the phosphorylated form of EIIA$^{Glc}$ cannot transfer its phosphate group to glucose and therefore it remains in its phosphorylated state. The unphosphorylated EIIA$^{Glc}$ mediates the phenomenon generally known as carbon catabolite repression (CCR). Under CCR, when glucose is present in the growth medium, the transport and/or utilization of other carbohydrates in the medium is prevented until the glucose in the medium is decreased to a low concentration. The carbon catabolite repression results from the inhibitory effect of unphosphorylated EIIA$^{Glc}$ on permease systems or other systems of carbon source utilization. A number of permeases involved in the carbohydrate transport are known to be inhibited by unphosphorylated EIIA$^{Glc}$, for example, LacY or lactose permease. In addition, the unphosphorylated EIIA$^{Glc}$ is known to have a negative effect on the transcription of number of genes involved in carbohydrate transport and metabolism through its influence on the adenylate cyclase system.

Strain KJ122, good succinate producer, contains a frameshift mutation in the ptsI gene, and this mutation is important for good succinate production. Thus it was surprising in the context of the current invention that further improvements in succinate production could be made by deleting ptsHI and galP, and then installing a facilitated diffusion system.

In another embodiment, the present invention provides a non-naturally occurring duplication of the crr gene that encodes the EIIA$^{Glc}$ protein. The inventors discovered that strains containing a ptsHI deletion, a galP mutation, and an installation of a functional glf gene, have an unexpected tendency to acquire a mutation in the crr gene which causes a decrease or elimination in function of the EIIA$^{Glc}$ protein, which in turn causes an unexpected undesirable decrease in succinate production parameters. Duplication of the crr gene by integrating a second copy of crr at a locus separate from the native crr locus solves this problem by greatly reducing the frequency of mutants that become phenotypically crr negative.

The present invention will be explained in detail below. An example bacterium belonging to the genus *Escherichia* of the present invention is a strain which is constructed from a parental strain that is not initially capable of using facilitated diffusion for sugar import, but which after genetic engineering as disclosed herein harbors a glf gene, and optionally an exogenous glk gene, and has the ability to use facilitated diffusion for import of glucose and fructose.

The exogenous genes introduced into the cell can be maintained within the cell on a self-replicating plasmid. A plasmid can be maintained through antibiotic selection or complementation of a chromosomal mutation. However, when the exogenous genes are maintained within the biocatalyst on a self-replicating plasmid within the cell, it is necessary to assure the there is no unnecessary waste of energy and materials leading to the inhibition of growth, and a decrease in the yield or productivity of the organic material being manufactured using the biocatalyst. Preferentially, the exogenous genes are integrated into the host chromosome so that there is no need to add any antibiotics to maintain the plasmids within the cell, and little or no metabolic burden is placed on the cell for plasmid maintenance. There are many possible locations within the cell for the integration of the exogenous genes. The preferential locations for integrating the exogenous genes within the E. coli chromosomal DNA include regions that do not encode an essential function for growth and product formation under commercial fermentation conditions.

When the exogenous genes are obtained as an operon, it is preferable to remove any possible negative regulatory genes or proteins from the operon. It is ideal to have only the genes and proteins that function positively in facilitated diffusion and metabolism. Thus, expression of a facilitated diffusion gene is preferably not inhibited by a repressor or by carbon catabolite repression.

The following examples are provided as a way of illustrating the present invention and not as a limitation.

Any bacterium that does not natively use a facilitated diffusion system for sugar import can be improved according to the present invention.

A bacterium of the present invention may be obtained by introduction of one or more genes that enables utilization of facilitated diffusion into a succinic acid producing strain such as KJ122 or other strain previously engineered to produce a desired chemical. Alternatively a bacterium of the present invention may be obtained by conferring an ability to produce succinic acid or other desired chemical to a bacterium in which utilization of facilitated diffusion has already been enabled by genetic engineering, and optionally by evolution. This latter alternative can be accomplished, for example, by following all the steps used for constructing KJ122 but starting with strain ATCC 9637 or a K-12 type E. coli strain, or any other safe E. coli strain, instead of starting with strain ATCC 8739.

Example 1

Construction of AC15, a Derivative of KJ122 that Contains the Glf and Glk Genes from Gene Cluster from Zymomonas mobilis CP4

All manipulations of DNA and plasmids, polymerase chain reaction (PCR), transformation, and chromosomal integration were accomplished by standard methods that are well known in the art. It is well known that DNA sequences can be cloned and joined together to form new combinations that cannot be easily found in nature. In addition to the more traditional methods involving restriction enzymes and DNA ligase, newer methods using recombineering in yeast, the so-called "Gibson Method" of in vitro splicing of DNA, or any other appropriate method can be used to construct such novel DNA sequences. The DNA fragments needed can be obtained from libraries of clones or by PCR from appropriate template DNA. It is also understood that many desired DNA sequences can be designed and synthesized from chemical precursors. Such a service is supplied by a number of commercial companies, for example DNA 2.0 and GeneArt (Invitrogen).

Plasmid pAC19 was constructed to contain an artificial operon containing the glf and glk genes from Z. mobilis, driven by the $P_{26}$ promoter from the Bacillus subtilis phage SP01. This operon was embedded between an upstream sequence homologous to the E. coli C tdcC gene and a downstream sequence homologous to the E. coli C tdcE gene, to foster integration into the tdcCDE locus of strains to be engineered. The cassette described above is carried on a low copy plasmid vector derived from pCL1921, which contains the pSC101 origin of replication and a spectinomycin resistance gene. The components for the cassette were obtained by PCR using appropriate synthetic DNA primers obtained from commercial suppliers such as Sigma and Integrated DNA Technologies (IDT). The source for the Zymononas genes was pLOI1740, which originally contained a zwf and edd gene in addition to the desired glf and glk genes. The glf, zwf, edd, glk cluster was transferred to pCL1921, and then the unnecessary zwf and edd genes were deleted by inside out PCR. The upstream and downstream tdc sequences were obtained by PCR from KJ122 chromosomal DNA as template. The $P_{26}$ promoter was obtained from bacteriophage SP01. The sequence of pAC19 is given as SEQ ID #1.

All constructions were done while growing strains on LB medium (10 grams Bacto-tryptone, 5 grams Bacto-yeast extract, and 5 grams sodium chloride) supplemented as appropriate with antibiotic or sucrose. To construct strain AC15, the cassette containing the artificial operon of pAC19 was integrated into the chromosome of strain WG53, using a two step gene replacement method previously described. The cat, sacB cassette for the first step was contained on plasmid pAC21, SEQ ID #2. pAC21 is similar to pAC19, except that the artificial operon is replaced with a cat, sacB cassette that contains a chloramphenicol resistance gene and a counterselectable sacB gene encoding levan sucrase. The transforming DNA was obtained by PCR form pAC21 for the first step and by PCR from pAC19 for the second step.

Strain WG53 was obtained by deleting the ptsH, ptsI, and galP genes from succinate producing strain KJ122, using a two step gene replacement method similar to that described in the above paragraph. The DNA sequence spanning the ptsHI deletion is given as SEQ ID #3. Note that this deletion leaves the crr gene intact, as well as native promoters that naturally exist upstream from the ptsH gene. The DNA sequence spanning the galP deletion is given as SEQ ID #4.

While intermediate strain WG53 grew extremely poorly on minimal glucose medium, strains KJ122 and AC15 grew well on minimal glucose medium, demonstrating that 1) the ptsHI and galP genes had been successfully deleted in WG53, and 2) the glf, glk cassette was functional in AC15 allowing glucose to be imported.

Example 2

Strain AC15 Produces Succinate as Well as Parent KJ122

Strains KJ122 and AC15 were grown under microaerobic condition in 7 liter fermentors (New Brunswick Scientific) at 39° C. using a minimal medium with glucose fed batch system. The starting volume of 3 liters contained potassium phosphate monobasic (18 mM), magnesium sulfate (2 mM), betaine (1.33 mM), trace elements, Antifoam 204 (8 ppm) and 25 g/l glucose. The pH was adjusted initially to pH 7.0 and thereafter was maintained at pH 6.5 as acid was produced by addition of the ammonium hydroxide/ammonium bicarbonate solution described below. The 150 ml inocula were grown aerobically and contained a minimal medium similar to the above described medium, except that glucose was at 20 g/l and calcium chloride was added to a final concentration of 0.1 mM. Agitation was set at 750 RPM (revolutions per minute). When glucose decreased to 5 g/l, a 650 g/l glucose feed was started and maintained at a rate aimed to keep the glucose concentration at about 5 g/l or less. The stock solution used for neutralization contained both ammonium hydroxide and ammonium bicarbonate (7 N NH$_4$OH and 3M NH$_4$HCO$_3$). AC15 was aerated at 35 ml/min, while KJ122 was not given air other than what was present in the head space, which was equilibrated with the atmosphere through a breathable sterile membrane filter. These were conditions that had been shown to work well for each strain. Sugars, succinate, and byproducts from 48 hour samples were assayed by HPLC. The results of averaged duplicates are shown in Table 1. AC15 produced about the same titer as parent KJ122, but the acetate byproduct was significantly lower, and the yield on glucose was higher for AC15.

Example 3

Spontaneous "Red Mutants" Derived from AC15

KJ122 is able to ferment lactose, as evidenced by formation of red colonies on MacConkey lactose plates (Beckton-Dickinson, Franklin Lakes, N.J.). However, AC15 does not ferment lactose, as evidence by producing "white" (beige) colonies on MacConkey lactose plates. This white colony phenotype of AC15 results from binding and inhibition of lactose permease (LacY) by unphosphorylated EIIA$^{Glc}$ protein. This white colony phenotype is present in all strains deleted for ptsHI, since the enzymes required to phosphorylate EIIA$^{Glc}$ are absent, and as a result, all EIIA$^{Glc}$ present in the cells remains unphosphorylated. Thus, ironically, E. coli ptsHI mutants are phenotypically Lac$^-$, even though lactose is not imported by the PTS system in E. coli.

The inventors noticed by chance that when MacConkey lactose plates were streaked with AC15 and allowed to incubate overnight at 37° C., and then for an extra day at room temperature (about 22° C.), a large number of red colonies emerged from the lawn of white colonies that had grown over the denser part of the streak. Upon restreaking of several of the red colonies, it was observed that two classes of red colonies had evolved. We shall call the first class "solid red", since the individual colonies were uniformly red across the entire colony. A second class shall be called "fried egg red", since the individual colonies were red in the center, but the outer portion of the colonies were white or beige. We shall call the strains giving rise to all types of red colonies on MacConkey lactose collectively "red mutants".

A white colony of AC15, and four red mutants, named AC15-R1, -R2, -R3, and -R4 (two of which are solid red and two of which are fried egg red), were tested for succinate production in 500 ml microaerobic fermentors (Fleakers, Corning Glass, Corning, N.Y.) using a medium and method similar to those described above for the 7 liter fermentors, with the differences being that the starting volume of the minimal medium was 200 ml, the glucose was all batched in the starting medium at 100 g/l, no glucose was fed, agitation was with a magnetic stirring bar at 350 RPM, and no air was deliberately introduced or removed. The results are shown in Table 2. The two fried egg mutants performed similarly to parent AC15, while the two solid red mutants performed significantly worse than parent AC15.

Genome sequencing of the parent AC15 and the four red mutants, using the Illumina HiSeq2000 system, revealed that both solid red mutants had acquired one mutation each, and both of these mutations were in the crr gene, which encodes EIIA$^{Glc}$. Both were judged to be null mutations. Both fried egg red mutants had acquired one mutation each, and both of these mutations were in the lactose operon. Both of these were judged to be mutations that would lead to a higher level of expression of the lactose operon (one was a mutation in the lacO operator, and the other was a frameshift in lacI, the gene that encodes the Lac repressor. All four mutations made sense in that they could explain the observed phenotype of increased ability to ferment lactose. The crr null mutations relieved the inhibition of the LacY permease, as would be expected, while the lactose operon mutations would be expected to overproduce LacY, allowing at least some escape from the inhibition. However, the crr null mutations clearly had an additional pleiotropic effect, causing a decrease in the cells' ability to produce succinate under our fermentation conditions. This was an unexpected effect that was not predicted.

Example 4

The Zymomonas mobilis Glk Gene is not Essential for Functioning of the Glf Gene in E. coli Plasmid pSS2 was constructed using methods similar to those described above for pAC19. The only differences between pSS2 and pAC19 is that the, Z. mobilis glk gene was deleted from the artificial operon. In other aspects, such as vector backbone, the promoter driving expression of glf, embedding the artificial operon in the tdc flanking sequences, and orientation of the various components, pSS2 is similar to pAC19. The DNA sequence of pSS2 is given as SEQ ID #5.

The artificial operon from pSS2 was integrated at the tdc locus of KJ122 as described above for the operon from pAC19, using the two step gene replacement method. Two isolates, which are presumably identical to each other were named SS8-9 and SS8-11. These two new strains were compared to AC15 in 500 ml microaerobic fermentors as described above in Example 3. The results, which are averages of duplicate fermentors assayed at 48 hours, are shown in Table 3. SS8-9 and SS8-11 both gave growth and succinate titers similar to that of AC15, while the acetate production of both SS8 isolates was somewhat lower than that of AC15. Thus, the Z. mobilis glk gene is unnecessary for functioning of the glf gene in this context, and the Z. mobilis glk gene might even be slightly harmful to the fermentation parameters. Presumably, the SS8 isolates are using the endogenous E. coli glk gene to phosphorylate glucose.

Example 5

Metabolic Evolution of Strain AC15

As noted above in Example 3, strain AC15 preferred to receive a higher level of aeration than parent KJ122 in 7 liter fermentors. In order to obtain a derivative of AC15 that could thrive on less air, AC15 was subjected to metabolic evolution in 500 ml fermentors with a starting volume of 200 ml and no deliberate supply of aeration. The conditions were microaerobic, since no measures were taken to remove oxygen. A small amount of air was assumed to leak into the fermentation vessels during the course of the evolution. The conditions for growth were as described in Example 3. After 48 hours of growth, the culture was diluted 1:100 into a fresh fermentor containing 200 ml of fresh medium, and this step was then repeated 40 more times. Each one of these inoculations to fresh medium shall be called a "transfer". Thus, the strain was subjected to a total of 41 transfers to fresh medium. Each transfer corresponds to about 7 generations of cell division. A sample of the liquid culture from the last transfer was plated on a MacConkey lactose agar petri plate, and a single white colony was chosen and named YSS41.

By varying the rate of aeration in 7 liter fermentors, it was determined that YSS41 performed well for succinate production with 5 ml/min of air, which was substantially less than the 35 ml/min required for optimal performance of the parent AC15. With 5 ml/min air flow, YSS41 produced 94 g/l succinate and 1.3 g/l acetate, for a succinate yield of 0.95 g/g glucose in 48 hours in a 7 liter fermentor.

YSS41 was compared to KJ122 for succinate production in a 20 liter fermentor. The fermentation protocol was similar to that described above for 7 liter fermentors, except that the starting volume was 9 liters, and the aeration rate was 25 ml/min for both strains, conditions that had been determined to be productive for both strains. The results for 48 hour samples are shown in Table 4. The succinate titer for YSS41 was 100 g/l (significantly higher than for KJ122), the acetate as 2.2 g/l (significantly lower than for KJ122), and the succinate yield was 0.95 g/g glucose (a little lower than for KJ122). Thus, the evolved strain YSS41 was able to perform well in a 20 liter fermentor with an aeration requirement that was no higher than for the ancestor strain KJ122.

Example 6

Stabilizing YSS41 Against Mutations in the Crr Gene

When streaked on MacConkey lactose plates, YSS41 still gave rise to red mutants, both of the solid red type and of the fried egg red type. The crr gene was sequenced for one isolate of each type. Strain MYR222, a fried egg type had a wild type crr gene sequence. MYR223, a solid red type, had an insertion element inserted in the crr open reading frame. The DNA sequence of the insertion element matched that of IS186. Thus, the pattern established for AC15 red mutants appeared to apply also to YSS41 red mutants. In 500 ml microaerobic fermentors, grown as in Example 4, MYR222 performed similarly to YSS41, while MYR223 performed more poorly (see Table 5). Thus the potential loss of performance due to accumulation of solid red mutants in a population remained a possibility with strain YSS41.

In order to solve this potential loss, a second copy of the crr gene was integrated into a site distant form the native crr locus. The crr gene, together with its flanking promoters and terminator were amplified by PCR using YSS41 chromosomal DNA as a template, and primers BY249 (SEQ ID #6) and BY250 (SEQ ID #7). The resulting blunt fragment was then ligated into a low copy plasmid derived from pCL1921 that contained a clone of a portion of the pflDC region from E. coli C at the unique BstZ171 restriction site in the pflD open reading frame. The pflDC genes are homologous to the pf7BA genes that encode pyruvate-formate lyase and the pyruvate-formate lyase activating enzyme. The pf7DC genes are not essential for E. coli, and deletion of either pflD or pflC has no significant effect on growth, so it was reasoned that insertion of a cassette at that locus would not have any negative consequence for growth or succinate production. The resulting low copy plasmid, pMH68, contains the crr gene from YSS41 embedded in flanking sequences from pflDC, in a low copy plasmid. The DNA sequence of pMH68 is given as SEQ ID #8.

The integration cassette from pMH68 was amplified by PCR using primers BY124 (SEQ ID #9) and BY125 (SEQ ID #10), which were the same primers used to clone the pflDC genes to begin with. The integration cassette was then integrated into the chromosome of YSS41, using the two step gene replacement method. The resulting strain was named MH141, which is now a merodiploid for crr, meaning that it contains two copies of a wild type crr gene in two distant locations on the chromosome, one at its native locus, and the second inserted in the pflD open reading frame.

As expected, strain MH141 produced white colonies on MacConkey lactose plates. If a heavy streak is made, and the plates are and allowed to incubate overnight at 37° C., and then for an extra day at room temperature, red colonies emerged from the lawn of white colonies that had grown over the denser part of the streak. However, the number of red mutants arising from MH141 was significantly lower than for a similar streak of YSS41 made on the same plate. 23 red mutants were picked from YSS41 and 12 red mutants were picked from MH141, and all were restreaked on MacConkey lactose plates. When scored for the type of red mutant, 12 of the 23 YSS41 red mutants were of the solid red type, while the other 11 of the 23 were of the fried egg type. In contrast, all 12 of the MH141 red mutants were of the fried egg type. Thus, by duplicating the crr gene in the chromosome, the rate of formation of the solid red mutants has been decreased by at least a factor of ten. One fried egg red mutant isolated from MH141 was named MH141-R1 and tested in 500 ml microaerobic fermentors as described above (see Table 5). Both MH141 and MH141-R1 performed similarly to parent YSS41 with respect to growth, succinate titer, and acetate titer. Thus, a more stable strain, MH141, has been constructed that uses facilitated diffusion for glucose import, and which produces a higher titer of succinate and a lower titer of the byproduct acetate when compared to the ancestor strain KJ122, which uses a the GalP system for glucose import.

Example 7

YSS41 Acquired Mutations in the Glf, Glk Cassette During Metabolic Evolution

The DNA sequences of the glf, glk expression cassettes in AC15 and YSS41 were determined. The regions were amplified by PCR and the resulting fragments were sequenced over the glf and glk genes and more than 200 base pairs upstream and downstream, by the dideoxy chain termination method. The sequenced region corresponds to bases 4976 to 7920 of pAC19, given in SEQ ID #1. Two mutations were found that were acquired during the evolution of YSS41. The first mutation was a G to A change at base number 7742 of SEQ ID #1. This base is in the 5' untranslated region of the glf, glk mRNA transcript, just upstream from the glf open reading frame, and results in a C to U change at base-22 relative to the ATG start codon, or +15 relative to the start of transcription, in the glf mRNA (messenger RNA). This mutation is expected to increase or decrease the rate of translation of the glf open reading frame. The second mutation was a G to A change at base number 6173 of SEQ ID #1. This base is in the 5' untranslated region just upstream from the glk open reading frame, and results in a C to U change at base-15 relative to the ATG start codon in the glk mRNA. This mutation is expected to increase or decrease the rate of translation of the glk open reading frame. Thus, the evolution of YSS41 resulted in a more optimal balance of expression between the glf and glk open reading frames, to result in a strain that outgrew and outperformed the parent strain AC15.

Other mutations that alter the rate of transcription or expression of the glf and glk genes, or that alter the concentration, specific activity, or stability of the glf and glk proteins, can similarly achieve a more optimal balance between the two encoded proteins will also benefit growth and production of a desired chemical. These other alternative mutations can be obtained by the using the method described above for YSS41. This method can also be applied to strains engineered to produce products other than succinate, where the ability to use facilitated diffusion or sugar import has been engineered into the strain.

Example 8

Fermentation of KJ122 and YSS41 after Optimization of Air Flow Rate for YSS41

The optimum air flow rate for parent strain KJ122 had been determined to be 25 ml/minute in a 20 liter fermentor. At the air flow rate of 25 ml/min, YSS41 strain showed better succinate titer and yield when compared to that of KJ122. Further improvement in succinate yield and titer with YSS41 strain was obtained by increasing the air flow rate to 50 ml/min. Thus the optimal air flow rate for YSS41 strain with reference to succinate yield and titer seems to be different from that of KJ122. Table 6 provides fermentation results in the 20 liter fermentor under the optimized air flow conditions for each strain. YSS41 outperformed parent KJ122 in titer, yield, and acetate byproduct formation. The initial volume of the fermentation was 9500 ml. After feeding glucose and neutralizing with base the final volume was 12500 ml.

REFERENCES

All references are listed for the convenience of the reader. Each reference is incorporated by reference in its entirety.
U.S. Pat. No. 5,602,030
U.S. Pat. No. 6,962,794
U.S. Pat. No. 7,220,561
U.S. Pat. No. 8,389,214
U.S. Pat. No. 8,476,041
US Patent Application Publication No. 20050079617
US Patent Application Publication No. 20090047719
US Patent Application Publication No. 20090253192
US Patent Application Publication No. 20100184171
European Patent Document No. EP20070715351
European Patent Document No. EP0785275B1
International Patent Application Publication No. WO 2010/115067
International Patent Application Publication No. WO2011/123154
International Patent Application Publication No. WO2012/018699

Altschul, S. F., Gish, W., Miller, W., Myers, E. W., and Lipman, D. J. (1990) Basic local alignment search tool, *J Mol Biol* 215, 403-410.

Altschul, S. F., Madden, T. L., Schaffer, A. A., Zhang, J., Zhang, Z., Miller, W., and Lipman, D. J. (1997) Gapped BLAST and PSI-BLAST: a new generation of protein database search programs, *Nucleic Acids Res* 25, 3389-3402.

Altschul, S. F., and Koonin, E. V. (1998) Iterated profile searches with PSI-BLAST—a tool for discovery in protein databases, *Trends Biochem Sci* 23, 444-447.

Altschul, S. F., Wootton, J. C., Gertz, E. M., Agarwala, R., Morgulis, A., Schaffer, A. A., and Yu, Y. K. (2005) Protein database searches using compositionally adjusted substitution matrices, *FEBS J* 272, 5101-5109.

Baba, T., Ara, T., Hasegawa, M., Takai, Y., Okumura, Y., Baba, M., Datsenko, K. A., Tomita, M., Wanner, B. L., and Mori, H. (2006) Construction of *Escherichia coli* K-12 in-frame, single-gene knockout mutants: the Keio collection, *Mol Syst Biol* 2, 2006 0008

Barnell, W. O., Yi, K. C., and Conway, T. (1990) Sequence and genetic organization of a *Zymomonas mobilis* gene cluster that encodes several enzymes of glucose metabolism, *J Bacteriol* 172, 7227-7240.

Gosset, G. (2005) Improvement of *Escherichia coli* production strains by modification of the phosphoenolpyruvate:sugar phosphotransferase system, *Microb Cell Fact* 4, 14.

Hogema, B. M., Arents, J. C., Bader, R., and Postma, P. W. (1999) Autoregulation of lactose uptake through the LacY permease by enzyme IIAGlc of the PTS in *Escherichia coli* K-12, *Mol Microbiol* 31, 1825-1833.

Jantama, K., Haupt, M. J., Svoronos, S. A., Zhang, X., Moore, J. C., Shanmugam, K. T., and Ingram, L. O. (2008) Combining metabolic engineering and metabolic evolution to develop nonrecombinant strains of *Escherichia coli* C that produce succinate and malate, *Biotechnol Bioeng* 99, 1140-1153

Jantama, K., Zhang, X., Moore, J. C., Shanmugam, K. T., Svoronos, S. A., and Ingram, L. O. (2008) Eliminating side products and increasing succinate yields in engineered strains of *Escherichia coli* C, *Biotechnol Bioeng* 101, 881-893.

Lee, G., Talkington, C., and Pero, J. (1980) Nucleotide sequence of a promoter recognized by *Bacillus subtilis* RNA polymerase, *Mol Gen Genet* 180, 57-65.

Lee, G., Hannett, N. M., Korman, A., and Pero, J. (1980) Transcription of cloned DNA from *Bacillus subtilis* phage SP01. Requirement for hydroxymethyluracil-containing DNA by phage-modified RNA polymerase, *J Mol Biol* 139, 407-422.

Lerner, C. G., and Inouye, M. (1990) Low copy number plasmids for regulated low-level expression of cloned genes in *Escherichia coli* with blue/white insert screening capability, *Nucleic Acids Res* 18, 4631.

Merryman, C., and Gibson, D. G. (2012) Methods and applications for assembling large DNA constructs, *Metab Eng* 14, 196-204.

Moran, C. P., Jr., Lang, N., LeGrice, S. F., Lee, G., Stephens, M., Sonenshein, A. L., Pero, J., and Losick, R. (1982) Nucleotide sequences that signal the initiation of transcription and translation in *Bacillus subtilis*, *Mol Gen Genet* 186, 339-346.

Mueckler, M., Caruso, C., Baldwin, S. A., Panico, M., Blench, I., Morris, H. R., Allard, W. J., Lienhard, G. E., and Lodish, H. F. (1985) Sequence and structure of a human glucose transporter, *Science* 229, 941-945.

Neidhardt, F. C., and Curtiss, R. (1996) *Escherichia coli* and *Salmonella: cellular and molecular biology*, 2nd ed., ASM Press, Washington, D.C.

Niu, W., Draths, K. M., and Frost, J. W. (2002) Benzene-free synthesis of adipic acid, *Biotechnol Prog* 18, 201-211.

Pao, S. S., Paulsen, I. T., and Saier, M. H., Jr. (1998) Major facilitator superfamily, *Microbiol Mol Biol Rev* 62, 1-34.

Parker, C., Peekhaus, N., Zhang, X., and Conway, T. (1997) Kinetics of Sugar Transport and Phosphorylation Influence Glucose and Fructose Cometabolism by *Zymomonas mobilis*, *Appl Environ Microbiol* 63, 3519-3525.

Rogers, P. L., Jeon, Y. J., Lee, K. J., and Lawford, H. G. (2007) *Zymomonas mobilis* for fuel ethanol and higher value products, *Adv Biochem Eng Biotechnol* 108, 263-288.

Sambrook, J. (1989) *Molecular Cloning: A Laboratory Manual*, Cold Spring Harbor Press, Cold Spring Harbor, N.Y.

Shanks, R. M., Kadouri, D. E., MacEachran, D. P., and O'Toole, G. A. (2009) New yeast recombineering tools for bacteria, *Plasmid* 62, 88-97.

Snoep, J. L., Arfman, N., Yomano, L. P., Fliege, R. K., Conway, T., and Ingram, L. O. (1994) Reconstruction of glucose uptake and phosphorylation in a glucose-negative mutant of *Escherichia coli* by using *Zymomonas mobilis* genes encoding the glucose facilitator protein and glucokinase, *J Bacteriol* 176, 2133-2135.

Tang, J., Zhu, X., Lu, J., Liu, P., Xu, H., Tan, Z., and Zhang, X. (2013) Recruiting alternative glucose utilization pathways for improving succinate production, *Appl Microbiol Biotechnol* 97, 2513-2520.

Weisser, P., Kramer, R., Sahm, H., and Sprenger, G. A. (1995) Functional expression of the glucose transporter of *Zymomonas mobilis* leads to restoration of glucose and fructose uptake in *Escherichia coli* mutants and provides evidence for its facilitator action, *J Bacteriol* 177, 3351-3354.

Zhang, X., Jantama, K., Shanmugam, K. T., and Ingram, L. O. (2009) Reengineering *Escherichia coli* for Succinate Production in Mineral Salts Medium, *Appl Environ Microbiol* 75, 7807-7813.

Zhang, X., Jantama, K., Moore, J. C., Jarboe, L. R., Shanmugam, K. T., and Ingram, L. O. (2009) Metabolic evolution of energy-conserving pathways for succinate production in *Escherichia coli*, *Proc Natl Acad Sci USA* 106, 20180-20185.

TABLE 1

Production of Succinate by AC15 in 7 Liter Fermentors

| Strain | Relevant genotype | Aeration ml/min | Succinate g/l | Acetate g/l | Yield g/g glucose |
|---|---|---|---|---|---|
| KJ122 | parent, ptsI*, galP+ | 0 | 87 | 5.2 | 0.83 |
| AC15 | KJ122, ΔptsHI, ΔgalP, $P_{26}$-glf, glk | 35 | 87 | 2.7 | 0.88 |

TABLE 2

Production of succinate by AC15 red mutants in 500 ml microaerobic fermentors

| Strain | Colony phenotype on MacConkey lactose | Succinate g/l | Acetate g/l | $OD_{600}$ | Mutation found |
|---|---|---|---|---|---|
| AC15 | white | 74 | 2.4 | 7.5 | none |
| AC15-R1 | solid red | 51 | 9.0 | 6.5 | crr Lys16 frameshift |
| AC15-R3 | solid red | 65 | 6.6 | 7.0 | crr Met1Ile |
| AC15-R2 | fried egg red | 73 | 2.4 | 8.0 | lacO G11A |
| AC15-R4 | fried egg red | 73 | 3.0 | 7.5 | lacI Asp300 frameshift |

TABLE 3

Succinate production by SS8 isolates in 500 ml microaerobic fermentors

| Strain | Relevant genotype | Succinate g/l | Acetate g/l | $OD_{600}$ |
|---|---|---|---|---|
| AC15 | KJ122, ΔptsHI, ΔgalP, $P_{26}$-glf, glk | 64 | 6.0 | 7.5 |
| SS8-9 | KJ122, ΔptsHI, ΔgalP, $P_{26}$-glf | 64 | 4.2 | 8.5 |
| SS8-11 | KJ122, ΔptsHI, ΔgalP, $P_{26}$-glf | 64 | 3.6 | 8.2 |

TABLE 4

Succinic acid production by YSS-41, in a 20 liter fermentor

| Strain | Relevant genotype | Air flow rate ml/min | Succinate g/l | Acetate g/l | Yield on glucose g/g |
|---|---|---|---|---|---|
| KJ122 | ptsI* | 25 | 87 | 6.8 | 1.00 |
| KJ122 | ptsI* | 25 | 85 | 6.8 | 0.98 |
| YSS41 | KJ122☐☐ΔptsHI, ΔgalP, $P_{26}$-glf, glk, evolved | 25 | 100. | 2.2 | 0.95 |

TABLE 5

Succinate production in 500 ml microaerobic fermentors by MH141, a merodiploid for crr+.

| Strain | Relevant genotype | Colony phenotype on MacConkey lactose | Succinate g/l | Acetate g/l | $OD_{600}$ |
|---|---|---|---|---|---|
| YSS41 | AC15, evolved, crr+ | white | 67 | 3.9 | 10.0 |
| MH141 | YSS41, ΔpflD::crr+ | white | 68 | 3.2 | 8.5 |

TABLE 6

Succinate production by *E. coli* strains KJ122 and YSS41 in 20 liter fermentors under optimized aeration conditions for both strains

| Strain | Air flow rate (ml/min) | Succinate titer (g/l) | Succinate yield on glucose (g/g) | Acetate titer (g/l) | Cell mass as OD600 |
|---|---|---|---|---|---|
| KJ122 | 25 | 81 | 0.86 | 3.9 | 12 |
| YSS41 | 50 | 96 | 0.98 | 2.5 | 13 |
| YSS41 | 25 | 93 | 0.98 | 2.5 | 13 |

SEQUENCE LISTING

<160> NUMBER OF SEQ ID NOS: 12

<210> SEQ ID NO 1
<211> LENGTH: 9430
<212> TYPE: DNA
<213> ORGANISM: Escherichia coli
<220> FEATURE:
<221> NAME/KEY: pAC19
<222> LOCATION: (1)..(9430)
<223> OTHER INFORMATION: Plasmid used to install a glf-glk casette at
the tdc locus of bacterial strain KJ122

<400> SEQUENCE: 1

```
gttgacagta agacgggtaa gcctgttgat gataccgctg ccttactggg tgcattagcc      60
agtctgaatg acctgtcacg ggataatccg aagtggtcag actggaaaat cagagggcag     120
gaactgctga acagcaaaaa gtcagatagc accacatagc agacccgcca taaaacgccc     180
tgagaagccc gtgacgggct tttcttgtat tatgggtagt ttccttgcat gaatccataa     240
aaggcgcctg tagtgccatt taccccccatt cactgccaga gccgtgagcg cagcgaactg     300
aatgtcacga aaagacagc gactcaggtg cctgatggtc ggagacaaaa ggaatattca     360
gcgatttgcc cgagcttgcg agggtgctac ttaagccttt agggttttaa ggtctgtttt     420
gtagaggagc aaacagcgtt tgcgacatcc ttttgtaata ctgcggaact gactaaagta     480
gtgagttata cacagggctg ggatctattc ttttatctt ttttattct ttctttattc     540
tataaattat aaccacttga atataaacaa aaaaaacaca caaggtcta gcggaattta     600
cagagggtct agcagaattt acaagttttc cagcaaaggt ctagcagaat ttacagatac     660
ccacaactca aaggaaaagg actagtaatt atcattgact agcccatctc aattggtata     720
gtgattaaaa tcacctagac caattgagat gtatgtctga attagttgtt ttcaaagcaa     780
atgaactagc gattagtcgc tatgacttaa cggagcatga aaccaagcta attttatgct     840
gtgtggcact actcaacccc acgattgaaa accctacaag gaaagaacgg acggtatcgt     900
tcacttataa ccaatacgct cagatgatga acatcagtag ggaaaatgct tatggtgtat     960
tagctaaagc aaccagagag ctgatgacga gaactgtgga aatcaggaat cctttggtta    1020
aaggctttga gattttccag tggacaaact atgccaagtt ctcaagcgaa aaattagaat    1080
tagtttttag tgaagagata ttgccttatc ttttccagtt aaaaaaattc ataaaatata    1140
atctggaaca tgttaagtct tttgaaaaca aatactctat gaggatttat gagtggttat    1200
taaaagaact aacacaaaag aaaactcaca aggcaaatat agagattagc cttgatgaat    1260
ttaagttcat gttaatgctt gaaaataact accatgagtt taaaaggctt aaccaatggg    1320
ttttgaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aattttttgag tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaca tatcaagggg aaaactgtcc    1800
atatgcacag atgaaaacgg tgtaaaaaag atagatacat cagagctttt acgagttttt    1860
ggtgcattta agctgttca ccatgaacag atcgacaatg taacagatga acagcatgta    1920
```

```
acacctaata gaacaggtga aaccagtaaa acaaagcaac tagaacatga aattgaacac   1980
ctgagacaac ttgttacagc tcaacagtca cacatagaca gcctgaaaca ggcgatgctg   2040
cttatcgaat caaagctgcc gacaacacgg gagccagtga cgcctcccgt ggggaaaaaa   2100
tcatggcaat tctggaagaa atagcgcttt cagccggcaa acctgaagcc ggatctgcga   2160
ttctgataac aaactagcaa caccagaaca gcccgtttgc gggcagcaaa acccgttatg   2220
cttgtaaacc gttttgtgaa aaattttta aataaaaaa ggggacctct agggtcccca    2280
attaattagt aatataatct attaaaggtc attcaaaagg tcatccaccg gatcaattcc   2340
cctgctcgcg caggctgggt gccaagctct cgggtaacat caaggcccga tccttggagc   2400
ccttgccctc ccgcacgatg atcgtgccgt gatcgaaatc cagatccttg acccgcagtt   2460
gcaaaccctc actgatccgc atgcccgttc catacagaag ctgggcgaac aaacgatgct   2520
cgccttccag aaaaccgagg atgcgaacca cttcatccgg ggtcagcacc accggcaagc   2580
gccgcgacgg ccgaggtctt ccgatctcct gaagccaggg cagatccgtg cacagcacct   2640
tgccgtagaa gaacagcaag gccgccaatg cctgacgatg cgtggagacc gaaaccttgc   2700
gctcgttcgc cagccaggac agaaatgcct cgacttcgct gctgcccaag gttgccgggt   2760
gacgcacacc gtggaaacgg atgaaggcac gaacccagtg gacataagcc tgttcggttc   2820
gtaagctgta atgcaagtag cgtatgcgct cacgcaactg gtccagaacc ttgaccgaac   2880
gcagcggtgg taacggcgca gtggcggttt tcatggcttg ttatgactgt tttttgggg    2940 tacagtctat gcctcgggca tccaagcagc aagcgcgtta cgccgtgggt cgatgtttga   3000
tgttatggag cagcaacgat gttacgcagc agggcagtcg ccctaaaaca aagttaaaca   3060
tcatgaggga agcggtgatc gccgaagtat cgactcaact atcagaggta gttggcgtca   3120
tcgagcgcca tctcgaaccg acgttgctgg ccgtacattt gtacggctcc gcagtggatg   3180
gcggcctgaa gccacacagt gatattgatt tgctggttac ggtgaccgta aggcttgatg   3240
aaacaacgcg gcgagctttg atcaacgacc ttttggaaac ttcggcttcc cctggagaga   3300
gcgagattct ccgcgctgta gaagtcacca ttgttgtgca cgacgacatc attccgtggc   3360
gttatccagc taagcgcgaa ctgcaatttg gagaatggca gcgcaatgac attcttgcag   3420
gtatcttcga gccagccacg atcgacattg atctggctat cttgctgaca aaagcaagag   3480
aacatagcgt tgccttggta ggtccagcgg cggaggaact cttttgatccg gttcctgaac   3540 aggatctatt tgaggcgcta atgaaacct taacgctatg gaactcgccg cccgactggg    3600
ctggcgatga gcgaaatgta gtgcttacgt tgtcccgcat ttggtacagc gcagtaaccg   3660
gcaaaatcgc gccgaaggat gtcgctgccg actgggcaat ggagcgcctg ccggcccagt   3720
atcagcccgt catacttgaa gctagacagg cttatcttgg acaagaagaa gatcgcttgg   3780
cctcgcgcgc agatcagttg gaagaatttg tccactacgt gaaaggcgag atcaccaagg   3840
tagtcggcaa ataatgtcta acaattcgtt caagccgacg ccgcttcgcg gcgcggctta   3900
actcaagcgt tagatgcact aagcacataa ttgctcacag ccaaactatc aggtcaagtc   3960
tgcttttatt attttaagc gtgcataata agccctacac aaattgggag atatatcatg   4020
aaaggctggc tttttcttgt tatcgcaata gttggcgaag taatcgcaac atccgcatta   4080
aaatctagcg agggctttac taagctgatc cggtggatga ccttttgaat gacctttaat   4140
agattatatt actaattaat tggggaccct agaggtcccc ttttttattt taaaaatttt   4200
ttcacaaaac ggtttacaag catacgttgg ccgattcatt aatgcagctg gcacgacagg   4260
tttcccgact ggaaagcggg cagtgagcgc aacgcaatta atgtgagtta gctcactcat   4320
```

```
taggcacccc aggctttaca ctttatgctt ccggctcgta tgttgtgtgg aattgtgagc   4380
ggataacaat ttcacacagg aaacagctat gaccatgatt acgccaagct tgcatgcctg   4440
caggtcgact ctagaggatc ccccccgccg ccgacagagt aataggtttt acttaatagc   4500
tcttcctgtc ccttccaggc agtgatccgc attccgttct catggcgagg caacatttcg   4560
ggatggaaga taatgttctt tgctacagga aaatcaacaa tatgcgcacc agatgccact   4620
ggcagccgcc cgctgcgcgt tactaactct ataaatgcag ggatctcatc aatgacaaca   4680
tcctgcggac tgtttcctgc cagtcccatg atgatggcga catccgtggc atggcctttg   4740
cccgtcagtg acaacgaccc gtacagatcg accacaatat ggctcgtcgc ggttaataag   4800
ccgctacttt ccagccgatc aataaaactt tttccggcat tcattggccc cacggtatgc   4860
gaactggagg gaccaatccc aattttgaaa atatcgaatg cactaatcat atccacaccc   4920
tcggattgcc gttcagtgaa gtggagcgga acgaccttac gaccgtcccg ctcacgaggc   4980
tttacgcact acgtactgcg atggcttcaa tttccagcgg gagggcggat ccactaatac   5040
aaaatatatc aaaagttaat aataatatta ttcttactta agactttttt gtcttcattt   5100
tttagtaaaa aatataaaaa aggccacctc ccgattttat cggaaggcag cctcttaaat   5160
tcagttcata atattaaaaa atattattca acttcagaat atttgttggc ataggcagct   5220
gccgcaccca acagtccagg ctgcggataa gtaatcaact taaccggaat cttggacatg   5280
acgcgttcaa agcgtccttt tgaaacaaag cgctgacgga aaccagattc tggcaaatgg   5340
gaagcgatac gaagaccgac accaccgcca ataacaacac tggttcgacc ctgtgccaaa   5400
gcaagatcac cagcgatagc gccaaggctc aagcagaagc gatccaaagc ggcttcagca   5460
aggttgtctt taccttccaa agccatctgc cataatttaa tatcatccag caagctgaac   5520
ggaacgcctt caatggcagc cagtgcttcg tagatattac caagacccgg ccagaaata   5580 atgcgttcga tagaaacgcg gcggaaacgt tcacgtaaac gtgccagaat tttgtcttca   5640
agtctgtcaa gcggagcaaa gtcgatatga ccgccttcag tttcgatgac gaaataacgg   5700
ccttcagtcc gcaacagatg ggcaacaccc aagcccgttc ccggaccaag aatagtgata   5760
acaccatcgc taggaagcgc ttcatcagga ccacaaatat gatccagata agaagaatcc   5820
atatgcgcaa ccgcgtgggc aaccgcgccg aagtcattga tcagaacatg cgtatcgatg   5880
tccagctttt cattcagagt agctggtctt aatacccaag ggttattggt aagttttaaa   5940
acttcaccat gaaccgggcc agcccatgca atagctgcgg cacgtggcag aggacgaccc   6000
agtttttcac cgaaacgttc ccaagctaac tgcaagctag catgttctgc cgttttaaaa   6060
gttgtttctt ctccaagaga aagaacccga ccattgctta cttccgcaat agagaaacgc   6120
gcatgcgttc caccgatgtc aatcgcaaca atttccataa taattccttt ctgaaatcag   6180
aaggctaccc aacaggtaaa ataagtccgc ccgctttata ccatcgttgt aaacaaaaag   6240
tataattggt taagacttat ctaaaaaaga caaaaggatt cagccaaagc aagtttaact   6300
acttctggga gcgccacatc tcctcgattt catccaggct ccgacctttg gtttccggca   6360
cgaagcgagc aacaatcaag ccacctaaga tacttaatgc tgcgaaaacg agataggaga   6420
aaccgtggtt gaaagtctga ttcaatgctg gagaaccatc ggcaacctta aacaggaagt   6480
taaccaagat attagctaac cattgtccgg taacagcgat aggcatagct gcgcccttga   6540
tggaactcgg gaacatttct gacagaacaa cccagcagac agggcccat gacataccaa   6600 agactgcaat ataaagaagc acagaagcca aggcaaaac accaccgact ttgaaccaga   6660
```

-continued

```
aacagcagcc taaaacagcc atcattgcag ccataccgag agcaccccaa ataagcagag    6720
gtttacggcc gaagcggtca acaacacggg aagcaatcat ggtgaagatg aagttcacaa    6780
caccgataga gatggtctgc aataatgccg tatcagctcc aaaacctaaa ttctggaaca    6840
tctgcggtgc ataatacagc acggcgttaa taccgactaa ctgctggaag gcagcaacgg    6900
atacaccggc aaaaacaacg gtgataccaa aagcaaacaa acctgcgctg cttttgtcca    6960
tggctttatc aaagccagct ttaatctttt gaatcgtcag attaggatcg gcttgcggtt    7020
ccagacgagc aaggattttg ctagcctcgg aatgacgtcc cttcatcacc aaccaatgcg    7080
gcgtatccgg tgcggttaac agcagcaata agaaggcaat accgatcagg ccttctgaag    7140
ccggagacca gcaccaacca ctggcattaa cccaatcgat agaaccgaaa tgagccagta    7200
accaggtaaa gatataaccg gttaaagcac ccgtcacaat ggccatctgc tgaccagaaa    7260
ccatctgacc acgtttgtct ggcggagcaa tttcagcaat ataggttggg gtcaaggttg    7320
aaacgacacc gatacctaaa ccggcaagaa accggaaaaa gcaaaaaatt tgtaaagccg    7380
aaccaccggt tccaaataat ttttcggtta acgcagcacc aaaaccggcg gcgacgaaac    7440
aaatggaact catcaacaat ccgccgcgac gaccgaagcg aataccaatc cagccagaca    7500
gcaaagaacc ggtaacacaa ccgaccaaaa cagcaacaac gaccatccca gaagggaag    7560 ccgcagccgt agcagacagg tgacgagggg caataaaatg gatatcaacc ggtgtaccga    7620
ttgcagcgat aaccgctgaa tcgtaaccga aaagcaagcc gcctatagca gcgattaggg    7680
ctagtcgcgt gactagaccc tgactacttt cagaactcat ggcgattcct ctccctctag    7740
agcgtcctgc tgttgttaag attattatac cacaccttgt agataaagtc aacaactttt    7800
tgcaaaattt ttcaggaatt ttagcagagg ttgttctgga tgtagaacaa acatctttc    7860 cgctcttgtg ctgttaggat atctttcttg gaagctaggt aggcctcgag ttatggcagt    7920
tggttaaaag gaaacaaaaa gaccgttttc acacaaaacg gtcttttcg atttctttt    7980 acagtcacag ccacttttgc accaattaag gccacgctgt catttaaact ccgttttcc    8040 agttcaaatg caattgcctt caatgcacct tcgtagctgt ggtgagccag cggtgctggc    8100
tctcccccat ttacggataa gaatgcattt tccgagttaa taccgtcggc aatacctgac    8160
attaatactt cacagtcgct ggcatcgagt acggaaaact taatcgaaga cgaaccacag    8220
ttaataacca aaacaaccgg aaattcattc atctctttc tcatcctgag ttacggatta    8280
aaacagtttg tatacgatgt tcaggatggt cagcagacca atcacggtaa caaacacgtt    8340
atccagacga ccacggtatt tcgccagaga cggcgcttta cggatggcat acatcggcaa    8400
caggcacagc agggatgcga taatcggtgc gcccatggct tcaatcaggt cgaggatgtt    8460
cgggttggcg taggcaacaa cccaggtgga gcccatgatg aagatcatgc tgagagtatt    8520
cagtttaccc agcgacactt tggttttgtc accttattaa ccgaacttca gaatcagacc    8580
attcaagcct tccagcgtcc ccagatagtg accgaagaaa gatttgaaga tagccacgag    8640
tgcgatgatg gaagccgcat attccagtgt aatcgcgaac gttgttttgg taccggtcat    8700
ggacgcaaag tggttagcca gataagaaag cactggaata ttctgcgctt tggcttccgc    8760
catgttggcc ggagacagag taaacaggca gctaaaggca aagaacatca ccactgcaac    8820
catcagcatg ctggcacgag aaatgatttg gaacattta cgttcggtga agtcgcgacc    8880
gaagtctttc tcatactctt cacgtttaga aaccacgaag gaagagacga ttggcgagaa    8940
gttaaaggag aaaaccatga tggaaatccc cagccagaca gtgatcagga taccgtcatg    9000
accggttaac gacagcgaac cgaggtcaac ctggtcgata actgcagagt tccagtaagg    9060
```

```
gatcagcgac aaagaaatca gcaccaggct ggcgataaac ggccatacca ggtagctcag    9120
ggtaccgagc tcgaattcac tggccgtcgt tttacaacgt cgtgactggg aaaaccctgg    9180
cgttacccaa cttaatcgcc ttgcagcaca tccccctttc gccagctggc gtaatagcga    9240
agaggcccgc accgatcgcc cttcccaaca gttgcgcagc ctgaatggcg aatggcgcct    9300
gatgcggtat tttctcctta cgcatctgtg cggtatttca caccgcatat ggtgcactct    9360
cagtacaatc tgctctgatg ccgcatagtt aagccagccc cgacacccgc caacacccgc    9420
tgacgaattc                                                            9430
```

<210> SEQ ID NO 2
<211> LENGTH: 9462
<212> TYPE: DNA
<213> ORGANISM: Escherichia coli
<220> FEATURE:
<221> NAME/KEY: pAC21
<222> LOCATION: (1)..(9462)
<223> OTHER INFORMATION: Pplasmid used to install a slectable and
      counterselectable cat-sacB cassette at the tdc locus of strain
      KJ122
<220> FEATURE:
<221> NAME/KEY: pAC21
<222> LOCATION: (1)..(9462)
<223> OTHER INFORMATION: Plasmid used to install a slectable and
      counterselectable cat-sacB cassette at the tdc locus of strain
      KJ122
<220> FEATURE:
<221> NAME/KEY: misc_feature
<222> LOCATION: (5924)..(5924)
<223> OTHER INFORMATION: n is a, c, g, or t

<400> SEQUENCE: 2

```
gttgacagta agacgggtaa gcctgttgat gataccgctg ccttactggg tgcattagcc      60
agtctgaatg acctgtcacg ggataatccg aagtggtcag actggaaaat cagagggcag    120
gaactgctga acagcaaaaa gtcagatagc accacatagc agacccgcca taaaacgccc    180
tgagaagccc gtgacgggct tttcttgtat tatgggtagt ttccttgcat gaatccataa    240
aaggcgcctg tagtgccatt tacccccatt cactgccaga gccgtgagcg cagcgaactg    300
aatgtcacga aaagacagc gactcaggtg cctgatggtc ggagacaaaa ggaatattca    360
gcgatttgcc cgagcttgcg agggtgctac ttaagccttt agggttttaa ggtctgtttt    420
gtagaggagc aaacagcgtt tgcgacatcc ttttgtaata ctgcggaact gactaaagta    480
gtgagttata cacagggctg ggatctattc tttttatctt tttttattct ttctttattc    540
tataaattat aaccacttga atataaacaa aaaaaacaca caaggtctca gcggaattta    600
cagagggtct agcagaattt acaagttttc cagcaaaggt ctagcagaat ttacagatac    660
ccacaactca aaggaaaagg actagtaatt atcattgact agcccatctc aattggtata    720
gtgattaaaa tcacctagac caattgagat gtatgtctga attagttgtt ttcaaagcaa    780
atgaactagc gattagtcgc tatgacttaa cggagcatga aaccaagcta attttatgct    840
gtgtggcact actcaacccc acgattgaaa accctacaag gaaagaacgg acggtatcgt    900
tcacttataa ccaatacgct cagatgatga acatcagtag ggaaaatgct tatggtgtat    960
tagctaaagc aaccagagag ctgatgacga gaactgtgga atcaggaat cctttggtta    1020 aaggctttga gattttccag tggacaaact atgccaagtt ctcaagcgaa aaattagaat    1080
tagtttttag tgaagagata ttgccttatc ttttccagtt aaaaaaattc ataaaatata    1140
atctggaaca tgttaagtct tttgaaaaca aatactctat gaggatttat gagtggttat    1200
```

```
taaaagaact aacacaaaag aaaactcaca aggcaaatat agagattagc cttgatgaat    1260
ttaagttcat gttaatgctt gaaaataact accatgagtt taaaaggctt aaccaatggg    1320
ttttgaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aattttttgag tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaca tatcaaaggg aaaactgtcc    1800
atatgcacag atgaaaacgg tgtaaaaaag atagatacat cagagctttt acgagttttt    1860
ggtgcattta aagctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa acccgttatg    2220
cttgtaaacc gttttgtgaa aaattttta aaataaaaaa ggggacctct agggtcccca    2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacgcgca gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact ctttgatccg gttcctgaac    3540
aggatctatt tgaggcgcta aatgaaacct taacgctatg gaactcgccg cccgactggg    3600
```

```
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt atttttaagc gtgcataata agccctacac aaattgggag atatatcatg    4020
aaaggctggc ttttcttgt tatcgcaata gttggcgaag taatcgcaac atccgcatta    4080
aaatctagcg agggctttac taagctgatc cggtggatga ccttttgaat gacctttaat    4140
agattatatt actaattaat tggggaccct agaggtcccc ttttttatt taaaaatttt    4200 ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgcatgcctg    4440
caggtcgact ctagaggatc cccccgccg ccgacagagt aataggtttt acttaatagc    4500
tcttcctgtc ccttccaggc agtgatccgc attccgttct catggcgagg caacatttcg    4560
ggatggaaga taatgttctt tgctacagga aaatcaacaa tatgcgcacc agatgccact    4620
ggcagccgcc cgctgcgcgt tactaactct ataaatgcag ggatctcatc aatgacaaca    4680
tcctgcggac tgtttcctgc cagtcccatg atgatggcga catccgtggc atggcctttg    4740
cccgtcagtg acaacgaccc gtacagatcg accacaatat ggctcgtcgc ggttaataag    4800
ccgctacttt ccagccgatc aataaaactt tttccggcat tcattggccc cacggtatgc    4860
gaactggagg gaccaatccc aattttgaaa atatcgaatg cactaatcat gtgacggaag    4920
atcacttcgc agaataaata aatcctggtg tccctgttga taccgggaag ccctgggcca    4980
acttttggcg aaaatgagac gttgatcggc acgtaagagg ttccaacttt caccataatg    5040
aaataagatc actaccgggc gtatttttg agttatcgag attttcagga gctaaggaag    5100
ctaaaatgga gaaaaaatc actggatata ccaccgttga tatatcccaa tggcatcgta    5160
aagaacattt tgaggcattt cagtcagttg ctcaatgtac ctataaccag accgttcagc    5220
tggatattac ggcctttta aagaccgtaa agaaaaataa gcacaagttt tatccggcct    5280
ttattcacat tcttgcccgc ctgatgaatg ctcatccgga attccgtatg gcaatgaaag    5340
acggtgagct ggtgatatgg gatagtgttc acccttgtta caccgttttc catgagcaaa    5400
ctgaaacgtt ttcatcgctc tggagtgaat accacgacga tttccggcag tttctacaca    5460
tatattcgca agatgtggcg tgttacggtg aaaacctggc ctatttccct aaagggttta    5520
ttgagaatat gttttcgtc tcagccaatc cctgggtgag tttcaccagt tttgatttaa    5580
acgtggccaa tatggacaac ttcttcgccc ccgttttcac catgggcaaa tattatacgc    5640
aaggcgacaa ggtgctgatg ccgctggcga ttcaggttca tcatgccgtt tgtgatggct    5700
tccatgtcgg cagaatgctt aatgaattac aacagtactg cgatgagtgg cagggcgggg    5760
cgtaattttt ttaaggcagt tattggtgcc cttaaacgcc tggtgctacg cctgaataag    5820
tgataataag cggatgaatg gcagaaattc gaaagcaaat tcgacccggt cgtcggttca    5880
gggcagggtc gttaaatagc cgcttatgtc tattgctggt ttantcggta cccggggatc    5940
```

```
gcggccgcgg accggatccc atcacatata cctgccgttc actattattt agtgaaatga   6000
gatattatga tattttctga attgtgatta aaaaggcaac tttatgccca tgcaacagaa   6060
actataaaaa atacagagaa tgaaaagaaa cagatagatt ttttagttct ttaggcccgt   6120
agtctgcaaa tcctttttatg attttctatc aaacaaaaga ggaaaataga ccagttgcaa   6180
```

```
gcggccgcgg accggatccc atcacatata cctgccgttc actattattt agtgaaatga   6000
gatattatga tattttctga attgtgatta aaaaggcaac tttatgccca tgcaacagaa   6060
actataaaaa atacagagaa tgaaaagaaa cagatagatt ttttagttct ttaggcccgt   6120
agtctgcaaa tccttttatg attttctatc aaacaaaaga ggaaaataga ccagttgcaa   6180
tccaaacgag agtctaatag aatgaggtcg aaaagtaaat cgcgcgggtt tgttactgat   6240
aaagcaggca agacctaaaa tgtgtaaagg gcaaagtgta tactttggcg tcacccctta   6300
catattttag gtcttttttt attgtgcgta actaacttgc catcttcaaa caggagggct   6360
ggaagaagca gaccgctaac acagtacata aaaaggaga catgaacgat gaacatcaaa   6420
aagtttgcaa acaagcaac agtattaacc tttactaccg cactgctggc aggaggcgca   6480
actcaagcgt ttgcgaaaga aacgaaccaa aagccatata aggaaacata cggcatttcc   6540
catattacac gccatgatat gctgcaaatc cctgaacagc aaaaaaatga aaatatcaa   6600
gttcctgaat tcgattcgtc cacaattaaa aatatctctt ctgcaaaagg cctggacgtt   6660
tgggacagct ggccattaca aaacgctgac ggcactgtcg caaactatca cggctaccac   6720
atcgtctttg cattagccgg agatcctaaa aatgcggatg acacatcgat ttacatgttc   6780
tatcaaaaag tcggcgaaac ttctattgac agctggaaaa acgctggccg cgtcttaaaa   6840
gacagcgaca aattcgatgc aaatgattct atcctaaaag accaaacaca gaatggtca    6900
ggttcagcca catttacatc tgacggaaaa atccgtttat tctacactga tttctccggt   6960
aaacattacg gcaaacaaac actgacaact gcacaagtta acgtatcagc atcagacagc   7020
tctttgaaca tcaacggtgt agaggattat aaatcaatct ttgacggtga cggaaaaacg   7080
tatcaaaatg tacagcagtt catcgatgaa ggcaactaca gctcaggcga caaccatacg   7140
ctgagagatc ctcactacgt agaagataaa ggccacaaat acttagtatt tgaagcaaac   7200
actggaactg aagatggcta ccaaggcgaa gaatctttat ttaacaaagc atactatggc   7260
aaaagcacat cattcttccg tcaagaaagt caaaaacttc tgcaaagcga taaaaaacgc   7320
acggctgagt tagcaaacgg cgctctcggt atgattgagc taaacgatga ttacacactg   7380
aaaaaagtga tgaaaccgct gattgcatct aacacagtaa cagatgaaat tgaacgcgcg   7440
aacgtctttta aaatgaacgg caaatggtac ctgttcactg actcccgcgg atcaaaaatg   7500
acgattgacg gcattacgtc taacgatatt tacatgcttg gttatgtttc taattcttta   7560
actggcccat acaagccgct gaacaaaact ggccttgtgt taaaaatgga tcttgatcct   7620
aacgatgtaa cctttactta ctcacacttc gctgtacctc aagcgaaagg aaacaatgtc   7680
gtgattacaa gctatatgac aaacagagga ttctacgcag acaaacaatc aacgtttgcg   7740
ccgagcttcc tgctgaacat caaaggcaag aaaacatctg ttgtcaaaga cagcatcctt   7800
gaacaaggac aattaacagt taacaaataa aaacgcaaaa gaaaatgcca atatcctatt   7860
ggcatttttct tttatttctt ccatttaaat ggatgcatgc gctagcggag tgtatactgg   7920
cttactatgt tggcactgat gagggtgtca gtgaagtgct tcagcctcgt gagcgggacg   7980
gtcgtaaggt cgttccgctc cacttcactg aacggcaatc cgagggtgtg gatccaatta   8040
aggccacgct gtcattaaa ttccgttttt ccagttcaaa tgcaattgcc ttcaatgcac   8100
cttcgtagct gtggtgagcc agcggtgctg gctctccccc atttacggat aagaatgcat   8160
tttccgagtt aataccgtcg gcaatacctg acattaatac ttcacagtcg ctggcatcga   8220
gtacggaaaa cttaatcgaa gacgaaccac agttaataac caaacaacc ggaaattcat   8280
tcatctcttt tctcatcctg agttacggat taaaacagtt tgtatacgat gttcaggatg   8340
```

```
gtcagcagac caatcacggt aacaaacacg ttatccagac gaccacggta tttcgccaga    8400
gacggcgctt tacggatggc atacatcggc aacaggcaca gcagggatgc gataatcggt    8460
gcgcccatgg cttcaatcag gtcgaggatg ttcgggttgg cgtaggcaac aacccaggtg    8520
gagcccatga tgaagatcat gctgagagta ttcagtttac ccagcgacac tttggttttg    8580
tcacctttat aaccgaactt cagaatcaga ccattcaagc cttccagcgt ccccagatag    8640
tgaccgaaga aagatttgaa gatagccacg agtgcgatga tggaagccgc atattccagt    8700
gtaatcgcga acgttgtttt ggtaccggtc atggacgcaa agtggttagc cagataagaa    8760
agcactggaa tattctgcgc tttggcttcc gccatgttgg ccggagacag agtaaacagg    8820
cagctaaagg caaagaacat caccactgca accatcagca tgctggcacg agaaatgatt    8880
tgggaacatt tacgttcggt gaagtcgcga ccgaagtctt tctcatactc ttcacgttta    8940
gaaaccacga aggaagagac gattggcgag aagttaaagg agaaaaccat gatggaaatc    9000
cccagccaga cagtgatcag gataccgtca tgaccggtta acgacagcga accgaggtca    9060
acctggtcga taactgcaga gttccagtaa gggatcagcg acaaagaaat cagcaccagg    9120
ctggcgataa acggccatac caggtagctc agggtaccga gctcgaattc actgccgtc    9180 gttttacaac gtcgtgactg ggaaaaccct ggcgttaccc aacttaatcg ccttgcagca    9240
catccccctt tcgccagctg gcgtaatagc gaagaggccc gcaccgatcg cccttcccaa    9300
cagttgcgca gcctgaatgg cgaatggcgc ctgatgcggt attttctcct tacgcatctg    9360
tgcggtattt cacaccgcat atggtgcact ctcagtacaa tctgctctga tgccgcatag    9420
ttaagccagc cccgacaccc gccaacaccc gctgacgaat tc                       9462

<210> SEQ ID NO 3
<211> LENGTH: 1091
<212> TYPE: DNA
<213> ORGANISM: Escherichia coli
<220> FEATURE:
<221> NAME/KEY: ptsHI
<222> LOCATION: (1)..(1091)
<223> OTHER INFORMATION: Sequence surrounding the deletion of ptsHI. The
      fusion junction is in between the nucleotide positions 425 and
      426.

<400> SEQUENCE: 3
gcaacagtaa tgccagcttg ttaaaaatgc gtaaaaaagc acctttttag gtgcttttt      60 gtggcctgct tcaaactttc gcccctcctg gcattgattc agcctgtcgg aactggtatt    120
taaccagact aattattttg atgcgcgaaa ttaatcgtta caggaaaagc caaagctgaa    180
tcgattttat gatttggttc aattcttcct ttagcggcat aatgtttaat gacgtacgaa    240
acgtcagcgg tcaacacccg ccagcaatgg actgtattgc gctcttcgtg cgtcgcgtct    300
gttaaaaact ggcgctaaca atacaggcta aagtcgaacc gccaggctag actttagttc    360
cacaacacta aacctataag ttggggaaat acaatgttcc agcaagaagt taccattacc    420
gctccacaat ctgctaatcc acgagatgcg gcccaattta ctgcttagga agagatcatg    480
ggtttgttcg ataaactgaa atctctggtt tccgacgaca agaaggatac cggaactatt    540
gagatcattg ctccgctctc tggcgagatc gtcaatatcg aagacgtgcc ggatgtcgtt    600
tttgcggaaa aaatcgttgg tgatggtatt gctatcaaac caacgggtaa caaaatggtc    660
gcgccagtag acggcaccat tggtaaaatc tttgaaacca accacgcatt ctctatcgaa    720
tctgatagcg gcgttgaact gttcgtccac ttcggtatcg acaccgttga actgaaaggc    780
```

| | |
|---|---|
| gaaggcttca agcgtattgc tgaagaaggt cagcgcgtga agttggcga tactgtcatt | 840 |
| gaatttgatc tgccgctgct ggaagagaaa gccaagtcta ccctgactcc ggttgttatc | 900 |
| tccaacatgg acgaaatcaa agaactgatc aaactgtccg gtagcgtaac cgtgggtgaa | 960 |
| accccggtta tccgcatcaa gaagtaattc tgccgcagtg aaaaatggcg cccatcggcg | 1020 |
| ccattttttt atgcttccgc cagcggcggc aaaatcaatt catcgctctc atgctgctgg | 1080 |
| gtgtagcgca t | 1091 |

```
<210> SEQ ID NO 4
<211> LENGTH: 66
<212> TYPE: DNA
<213> ORGANISM: Escherichia coli
<220> FEATURE:
<221> NAME/KEY: galP
<222> LOCATION: (1)..(66)
<223> OTHER INFORMATION: Sequence surrounding the deletion of galP gene.
      The fusion junction is in between the nucelotide positions 48 and
      49.

<400> SEQUENCE: 4
```

| | |
|---|---|
| atgcctgacg ctaaaaaaca ggggcggtca aacaaggcaa tgacgtttat aggcgctcac | 60 |
| gattaa | 66 |

```
<210> SEQ ID NO 5
<211> LENGTH: 8446
<212> TYPE: DNA
<213> ORGANISM: Escherichia coli
<220> FEATURE:
<221> NAME/KEY: pSS2
<222> LOCATION: (1)..(8446)
<223> OTHER INFORMATION: Plasmid used to install a glf cassette at the
      tdc lcous of bacterial strain KJ122.

<400> SEQUENCE: 5
```

| | |
|---|---|
| gttgacagta agacgggtaa gcctgttgat gataccgctg ccttactggg tgcattagcc | 60 |
| agtctgaatg acctgtcacg ggataatccg aagtggtcag actggaaaat cagagggcag | 120 |
| gaactgctga acagcaaaaa gtcagatagc accacatagc agacccgcca taaaacgccc | 180 |
| tgagaagccc gtgacgggct tttcttgtat tatgggtagt ttccttgcat gaatccataa | 240 |
| aaggcgcctg tagtgccatt tacccccatt cactgccaga gccgtgagcg cagcgaactg | 300 |
| aatgtcacga aaaagacagc gactcaggtg cctgatggtc ggagacaaaa ggaatattca | 360 |
| gcgatttgcc cgagcttgcg agggtgctac ttaagccttt agggttttaa ggtctgtttt | 420 |
| gtagaggagc aaacagcgtt tgcgacatcc ttttgtaata ctgcggaact gactaaagta | 480 |
| gtgagttata cacagggctg ggatctattc ttttttatctt tttttattct ttctttattc | 540 |
| tataaattat aaccacttga atataaacaa aaaaaacaca caaggtctag cggaattta | 600 |
| cagagggtct agcagaattt acaagttttc cagcaaaggt ctagcagaat ttacagatac | 660 |
| ccacaactca aaggaaaagg actagtaatt atcattgact agcccatctc aattggtata | 720 |
| gtgattaaaa tcacctagac caattgagat gtatgtctga attagttgtt ttcaaagcaa | 780 |
| atgaactagc gattagtcgc tatgacttaa cggagcatga aaccaagcta attttatgct | 840 |
| gtgtggcact actcaacccc acgattgaaa accctacaag gaaagaacgg acggtatcgt | 900 |
| tcacttataa ccaatacgct cagatgatga acatcagtag ggaaaatgct tatggtgtat | 960 |
| tagctaaagc aaccagagag ctgatgacga gaactgtgga atcaggaat cctttggtta | 1020 |
| aaggctttga gattttccag tggacaaact atgccaagtt ctcaagcgaa aaattagaat | 1080 |

```
tagttttag tgaagagata ttgccttatc ttttccagtt aaaaaaattc ataaaatata    1140
atctggaaca tgttaagtct tttgaaaaca aatactctat gaggatttat gagtggttat    1200
taaaagaact aacacaaaag aaaactcaca aggcaaatat agagattagc cttgatgaat    1260
ttaagttcat gttaatgctt gaaaataact accatgagtt taaaaggctt aaccaatggg    1320
ttttgaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aattttgag tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaga tatcaaaggg aaaactgtcc    1800
atatgcacag atgaaaacgg tgtaaaaaag atagatacat cagagctttt acgagttttt    1860
ggtgcattta agctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa acccgttatg    2220
cttgtaaacc gttttgtgaa aaaattttta aataaaaaa ggggacctct agggtcccca    2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacgcgca gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
```

```
aacatagcgt tgccttggta ggtccagcgg cggaggaact ctttgatccg gttcctgaac    3540
aggatctatt tgaggcgcta aatgaaacct taacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt atttttaagc gtgcataata agccctacac aaattgggag atatatcatg    4020
aaaggctggc tttttcttgt tatcgcaata gttggcgaag taatcgcaac atccgcatta    4080
aaatctagcg agggctttac taagctgatc cggtggatga ccttttgaat gacctttaat    4140
agattatatt actaattaat tgggaccct  agaggtcccc ttttttattt taaaaatttt    4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgcatgcctg    4440
caggtcgact ctagaggatc cccccgccg ccgacagagt aataggtttt acttaatagc     4500
tcttcctgtc ccttccaggc agtgatccgc attccgttct catggcgagg caacatttcg    4560
ggatggaaga taatgttctt tgctacagga aaatcaacaa tatgcgcacc agatgccact    4620
ggcagccgcc cgctgcgcgt tactaactct ataaatgcag ggatctcatc aatgacaaca    4680
tcctgcggac tgtttcctgc cagtcccatg atgatggcga catccgtggc atggcctttg    4740
cccgtcagtg acaacgaccc gtacagatcg accacaatat ggctcgtcgc ggttaataag    4800
ccgctacttt ccagccgatc aataaaactt tttccggcat tcattggccc cacggtatgc    4860
gaactggagg gaccaatccc aattttgaaa atatcgaatg cactaatcat atccacaccc    4920
tcggattgcc gttcagtgaa gtggagcgga acgaccttac gaccgtcccg ctcacgaggc    4980
tttacgcact acgtactgcg atggcttcaa tttccagcgg gagggcggat ccactaatac    5040
aaaatatatc aaaagttaat aataatatta ttcttactta agacttttt gtcttcattt     5100 tttagtaaaa aatataaaaa aggccacctc ccgatttat cggaaggcag cctcttaaat     5160
tcagttcata atattaaaaa atattattca acttcagatt atttgttggc ataggcagcg    5220
ctccgcccgc tttataccat cgttgtaaac aaaagtata  attggttaag acttatctaa    5280
aaaagacaaa aggattcagc caaagcaagt ttaactactt ctgggagcgc cacatctcct    5340
cgatttcatc caggctccga cctttggttt ccggcacgaa gcgagcaaca atcaagccac    5400
ctaagatact taatgctgcg aaaacgagat aggagaaacc gtggttgaaa gtctgattca    5460
atgctggaga accatcggca accttaaaca ggaagttaac caagatatta gctaaccatt    5520
gtccggtaac agcgataggc atagctgcgc ccttgatgga actcgggaac atttctgaca    5580
gaacaaccca gcagacaggg ccccatgaca taccaaagac tgcaatataa agaagcacag    5640
aagccaaagg caaaacacca ccgactttga accagaaaca gcagcctaaa acagccatca    5700
ttgcagccat accgagagca ccccaaataa gcagagtttt acggccgaag cggtcaacaa    5760
cacgggaagc aatcatggtg aagatgaagt tcacaacacc gatagagatg gtctgcaata    5820
```

```
atgccgtatc agctccaaaa cctaaattct ggaacatctg cggtgcataa tacagcacgg    5880
cgttaatacc gactaactgc tggaaggcag caacggatac accggcaaaa acaacggtga    5940
taccaaaagc aaacaaacct gcgctgcttt tgtccatggc tttatcaaag ccagctttaa    6000
tcttttgaat cgtcagatta ggatcggctt gcggttccag acgagcaagg attttgctag    6060
cctcggaatg acgtcccttc atcaccaacc aatgcggcgt atccggtgcg gttaacagca    6120
gcaataagaa ggcaataccg atcaggcctt ctgaagccgg agaccagcac caaccactgg    6180
cattaaccca atcgatagaa ccgaaatgag ccagtaacca ggtaaagata taaccggtta    6240
aagcacccgt cacaatggcc atctgctgac cagaaaccat ctgaccacgt tgtctggcg     6300 gagcaatttc agcaatatag gttggggtca aggttgaaac gacaccgata cctaaaccgg    6360
caagaaaccg gaaaaagcaa aaatttgta aagccgaacc accggttcca ataattttt     6420 cggttaacgc agcaccaaaa ccggcggcga cgaaacaaat ggaactcatc aacaatccgc    6480
cgcgacgacc gaagcgaata ccaatccagc cagacagcaa agaaccggta acacaaccga    6540
ccaaaacagc aacaacgacc atcccagaaa gggaagccgc agccgtagca gacaggtgac    6600
gaggggcaat aaaatggata tcaaccggtg taccgattgc agcgataacc gctgaatcgt    6660
aaccgaaaag caagccgcct atagcagcga ttagggctag tcgcgtgact agaccctgac    6720
tactttcaga actcatggcg attcctctcc ctctagagcg tcctgctgtt gttaagatta    6780
ttataccaca ccttgtagat aaagtcaaca acttttttgca aaattttca ggaattttag     6840 cagaggttgt tctggatgta gaacaaaaca tctttccgct cttgtgctgt taggatatct    6900
ttcttggaag ctaggtaggc ctcgagttat ggcagttggt taaaaggaaa caaaaagacc    6960
gttttcacac aaaacggtct ttttcgattt cttttttacag tcacagccac ttttgcacca    7020
attaaggcca cgctgtcatt taaactccgt ttttccagtt caaatgcaat tgccttcaat    7080
gcaccttcgt agctgtggtg agccagcggt gctggctctc ccccatttac ggataagaat    7140
gcattttccg agttaatacc gtcggcaata cctgacatta atacttcaca gtcgctggca    7200
tcgagtacgg aaaacttaat cgaagacgaa ccacagttaa taaccaaaac aaccggaaat    7260
tcattcatct cttttctcat cctgagttac ggattaaaac agtttgtata cgatgttcag    7320
gatggtcagc agaccaatca cggtaacaaa cacgttatcc agacgaccac ggtatttcgc    7380
cagagacggc gctttacgga tggcatacat cggcaacagg cacagcaggg atgcgataat    7440
cggtgcgccc atggcttcaa tcaggtcgag gatgttcggg ttggcgtagg caacaaccca    7500
ggtggagccc atgatgaaga tcatgctgag agtattcagt ttacccagcg acactttggt    7560
tttgtcacct ttataaccga acttcagaat cagaccattc aagccttcca gcgtcccag     7620 atagtgaccg aagaaagatt tgaagatagc cacgagtgcg atgatggaag ccgcatattc    7680
cagtgtaatc gcgaacgttg ttttggtacc ggtcatggac gcaaagtggt tagccagata    7740
agaaagcact ggaatattct gcgctttggc ttccgccatg ttggccggag acagagtaaa    7800
caggcagcta aaggcaaaga acatcaccac tgcaaccatc agcatgctgg cacgagaaat    7860
gatttgggaa catttacgtt cggtgaagtc gcgaccgaag tctttctcat actcttcacg    7920
tttagaaacc acgaaggaag agacgattgg cgagaagtta aggagaaaa ccatgatgga     7980 aatccccagc cagacagtga tcaggatacc gtcatgaccg gttaacgaca gcgaaccgag    8040
gtcaacctgg tcgataactg cagagttcca gtaagggatc agcgacaaag aaatcagcac    8100
caggctggcg ataaacggcc ataccaggta gctcagggta ccgagctcga attcactggc    8160
cgtcgtttta caacgtcgtg actgggaaaa ccctggcgtt acccaactta atcgccttgc    8220
```

```
agcacatccc cctttcgcca gctggcgtaa tagcgaagag gcccgcaccg atcgcccttc    8280
ccaacagttg cgcagcctga atggcgaatg gcgcctgatg cggtattttc tccttacgca    8340
tctgtgcggt atttcacacc gcatatggtg cactctcagt acaatctgct ctgatgccgc    8400
atagttaagc cagccccgac acccgccaac acccgctgac gaattc                   8446

<210> SEQ ID NO 6
<211> LENGTH: 31
<212> TYPE: DNA
<213> ORGANISM: Artificial Sequence
<220> FEATURE:
<223> OTHER INFORMATION: PCR Primer BY249 for amplifying and cloning the
      crr gene of YSS41, together with BY249.

<400> SEQUENCE: 6
gggcaacagt aatgccagct tgttaaaaat g                                   31

<210> SEQ ID NO 7
<211> LENGTH: 25
<212> TYPE: DNA
<213> ORGANISM: Artificial Sequence
<220> FEATURE:
<223> OTHER INFORMATION: PCR Primer BY250 for amplifying and cloning the
      crr gene of YSS41 together with BY249.

<400> SEQUENCE: 7
gggcgctaca cccagcagca tgaga                                          25

<210> SEQ ID NO 8
<211> LENGTH: 8937
<212> TYPE: DNA
<213> ORGANISM: Escherichia coli
<220> FEATURE:
<221> NAME/KEY: pMH68
<222> LOCATION: (1)..(8937)
<223> OTHER INFORMATION: Plasmid used to install a second copy of the
      crr gene from YSS41 at the pflD locus.

<400> SEQUENCE: 8
gttgacagta agacgggtaa gcctgttgat gataccgctg ccttactggg tgcattagcc    60
agtctgaatg acctgtcacg ggataatccg aagtggtcag actggaaaat cagagggcag    120
gaactgctga acagcaaaaa gtcagatagc accacatagc agaccgcca taaaacgccc    180 tgagaagccc gtgacgggct tttcttgtat tatgggtagt ttccttgcat gaatccataa    240
aaggcgcctg tagtgccatt taccccatt cactgccaga gccgtgagcg cagcgaactg    300
aatgtcacga aaagacagc gactcaggtg cctgatggtc ggagacaaaa ggaatattca    360
gcgatttgcc cgagcttgcg agggtgctac ttaagccttt agggttttaa ggtctgtttt    420
gtagaggagc aaacagcgtt tgcgacatcc ttttgtaata ctgcggaact gactaaagta    480
gtgagttata cacagggctg gatctattc tttttatctt ttttattct ttctttattc    540 tataaattat aaccacttga atataaacaa aaaaacaca caaaggtcta gcggaattta    600 cagggtct agcagaattt acaagttttc cagcaaaggt ctagcagaat ttacagatac    660
ccacaactca aaggaaaagg actagtaatt atcattgact agcccatctc aattggtata    720
gtgattaaaa tcacctagac caattgagat gtatgtctga attagttgtt ttcaaagcaa    780
atgaactagc gattagtcgc tatgacttaa cggagcatga aaccaagcta attttatgct    840
gtgtggcact actcaacccc cgattgaaa accctacaag gaaagaacgg acggtatcgt    900
tcacttataa ccaatacgct cagatgatga acatcagtag ggaaaatgct tatggtgtat    960
```

```
tagctaaagc aaccagagag ctgatgacga gaactgtgga aatcaggaat cctttggtta      1020
aaggctttga gattttccag tggacaaact atgccaagtt ctcaagcgaa aaattagaat      1080 tagttttag tgaagagata ttgccttatc ttttccagtt aaaaaaattc ataaaatata       1140
atctggaaca tgttaagtct tttgaaaaca aatactctat gaggatttat gagtggttat      1200
taaaagaact aacacaaaag aaaactcaca aggcaaatat agagattagc cttgatgaat      1260
ttaagttcat gttaatgctt gaaaataact accatgagtt taaaaggctt aaccaatggg      1320
ttttgaaacc aataagtaaa gatttaaaca cttacagcaa tatgaaattg gtggttgata      1380
agcgaggccg cccgactgat acgttgattt ccaagttga actagataga caaatggatc       1440
tcgtaaccga acttgagaac aaccagataa aaatgaatgg tgacaaaata ccaacaacca      1500
ttacatcaga ttcctaccta cgtaacggac taagaaaaac actacacgat gctttaactg      1560
caaaaattca gctcaccagt tttgaggcaa aattttgag tgacatgcaa agtaagcatg        1620
atctcaatgg ttcgttctca tggctcacgc aaaaacaacg aaccacacta gagaacatac      1680
tggctaaata cggaaggatc tgaggttctt atggctcttg tatctatcag tgaagcatca      1740
agactaacaa acaaaagtag aacaactgtt caccgttaga tatcaaaggg aaaactgtcc      1800
atatgcacag atgaaaacgg tgtaaaaaag atagatacat cagagctttt acgagttttt      1860
ggtgcattta agctgttca ccatgaacag atcgacaatg taacagatga acagcatgta       1920
acacctaata gaacaggtga aaccagtaaa acaaagcaac tagaacatga aattgaacac      1980
ctgagacaac ttgttacagc tcaacagtca cacatagaca gcctgaaaca ggcgatgctg      2040
cttatcgaat caaagctgcc gacaacacgg gagccagtga cgcctcccgt ggggaaaaaa      2100
tcatggcaat tctggaagaa atagcgcttt cagccggcaa acctgaagcc ggatctgcga      2160
ttctgataac aaactagcaa caccagaaca gcccgtttgc gggcagcaaa acccgttatg     2220
cttgtaaacc gttttgtgaa aaatttttta aataaaaaa ggggacctct agggtcccca       2280
attaattagt aatataatct attaaaggtc attcaaaagg tcatccaccg gatcaattcc      2340
cctgctcgcg caggctgggt gccaagctct cgggtaacat caaggcccga tccttggagc     2400
ccttgccctc ccgcacgatg atcgtgccgt gatcgaaatc cagatccttg acccgcagtt     2460
gcaaaccctc actgatccgc atgcccgttc catacagaag ctgggcgaac aaacgatgct     2520
cgccttccag aaaaccgagg atgcgaacca cttcatccgg ggtcagcacc accggcaagc     2580
gccgcgacgg ccgaggtctt ccgatctcct gaagccaggg cagatccgtg cacagcacct     2640
tgccgtagaa gaacagcaag gccgccaatg cctgacgatg cgtggagacc gaaaccttgc     2700
gctcgttcgc cagccaggac agaaatgcct cgacttcgct gctgcccaag gttgccgggt     2760
gacgcacacc gtgaaacgg atgaaggcac gaacccagtg gacataagcc tgttcggttc       2820
gtaagctgta atgcaagtag cgtatgcgct cacgcaactg gtccagaacc ttgaccgaac     2880
gcagcggtgg taacgcgca gtggcggttt catggcttg ttatgactgt ttttttgggg        2940
tacagtctat gcctcgggca tccaagcagc aagcgcgtta cgccgtgggt cgatgtttga     3000
tgttatggag cagcaacgat gttacgcagc agggcagtcg ccctaaaaca aagttaaaca     3060
tcatgaggga agcggtgatc gccgaagtat cgactcaact atcagaggta gttggcgtca     3120
tcgagcgcca tctcgaaccg acgttgctgg ccgtacattt gtacggctcc gcagtggatg     3180
gcggcctgaa gccacacagt gatattgatt tgctggttac ggtgaccgta aggcttgatg     3240
aaacaacgcg gcgagctttg atcaacgacc ttttggaaac ttcggcttcc cctggagaga     3300
```

```
gcgagattct ccgcgctgta gaagtcacca ttgttgtgca cgacgacatc attccgtggc   3360
gttatccagc taagcgcgaa ctgcaatttg gagaatggca gcgcaatgac attcttgcag   3420
gtatcttcga gccagccacg atcgacattg atctggctat cttgctgaca aaagcaagag   3480
aacatagcgt tgccttggta ggtccagcgg cggaggaact cttttgatccg gttcctgaac   3540 aggatctatt tgaggcgcta aatgaaacct taacgctatg gaactcgccg cccgactggg   3600
ctggcgatga gcgaaatgta gtgcttacgt tgtcccgcat ttggtacagc gcagtaaccg   3660
gcaaaatcgc gccgaaggat gtcgctgccg actgggcaat ggagcgcctg ccggcccagt   3720
atcagcccgt catacttgaa gctagacagg cttatcttgg acaagaagaa gatcgcttgg   3780
cctcgcgcgc agatcagttg gaagaatttg tccactacgt gaaaggcgag atcaccaagg   3840
tagtcggcaa ataatgtcta acaattcgtt caagccgacg ccgcttcgcg cgcggcttta   3900
actcaagcgt tagatgcact aagcacataa ttgctcacag ccaaactatc aggtcaagtc   3960
tgcttttatt atttttaagc gtgcataata agccctacac aaattgggag atatatcatg   4020
aaaggctggc ttttcttgt tatcgcaata gttggcgaag taatcgcaac atccgcatta   4080
aaatctagcg agggctttac taagctgatc cggtggatga cctttttgaat gaccttttaat   4140 agattatatt actaattaat tggggacccct agaggtcccc tttttttattt taaaaatttt   4200 ttcacaaaac ggtttacaag catacgttgg ccgattcatt aatgcagctg gcacgacagg   4260
tttcccgact ggaaagcggg cagtgagcgc aacgcaatta atgtgagtta gctcactcat   4320
taggcacccc aggctttaca ctttatgctt ccggctcgta tgttgtgtgg aattgtgagt   4380
gccaataccc gtgaaatctc gctggagcgg gcgctgcttt ataccgccag ccatcggcaa   4440
accgaaggcg aaccggtgat attgcgccgg gcgaaagcaa cagcgtatat ccttgaacat   4500
gttgaaattt cgattcgtga tgaagaactg attgccggta accgcaccgt aaaaccgcgc   4560
gccgggatta tgtcgccgga aatggaccct tactggctgc tgaagagct ggatcaattc   4620 ccgacgcgtc cgcaggaccg cttttgctatc agcaagaag ataaacgtat ctaccgcgaa   4680
gagttgttcc cgtactggga aaaacgttcg atgaaagatt tcatcaacgg gcagatgaca   4740
gatgaagtaa aagccgcgac cagcacgcag attttcagca tcaaccagac agataaaggc   4800
caggggcaca ttattattga ttacccacgc ctgctgaatc acgggctggg ggagctggta   4860
gcacagatgc agcaacattg tcagcaacag ccggagaatc acttttatca ggcagcgctg   4920
ttactgctgg aagcctcgca gaaacacatt ttgcgttacg ccgaactggc ggaaacgatg   4980
gcggcaaact gcacagatgc ccagcgtcgc gaagagctgc tgactattgc ggagatctcc   5040
cgccataacg cgcaacataa gccgcagacg ttctggcagg cgtgccagtt attctggtac   5100
atgaacatca ttctgcaata cgaatccaac gccagttcgc tatcgttggg gcgcttcgac   5160
cagtatatgt tgccgttcta tcagacatca ttaacccagg gcgaagatgc ggcgttcctg   5220
aaagaactgc tcgaatcttt atgggtgaaa tgcaacgaca tcgtgctgtt gcgctccacc   5280
agcagcgcgc gttatttcgc cggtttcccg accggctata ccgcactgct cggcgggtta   5340
accgagaacg gacgtagcgc ggtgaacgtg ctttcgttcc tttgccttga cgcctatcaa   5400
agcgtgcaat taccgcaacc gaacctcggc gtgcgcacta acgccttgat cgacacgccg   5460
ttcctgatga aaaccgccga aaccattcgc ctcggcaccg gtattccgca aatctttaac   5520
gatgaagtgg tggtgccagc gttcctcaac cgtggcgttt cgctggaaga tgcgcgcgac   5580
tattccgtag tgggctgtgt ggaattatct attcccggca gaacctacgg cttgcatgac   5640
atcgcgatgt ttaacctgct gaaagtgatg gaaatctgcc tgcatgaaaa tgaaggcaat   5700
```

-continued

```
gccgcgctga cttatgaagg tttactggaa cagatccgtg ccaagatcag ccactacatc    5760
accctgatgg ttgaaggcag taatatttgc gatatcggcc atcgcgactg ggcacctgta    5820
ccgctgctct cgtctttat cagcgattgt ctggaaaaag gccgcgatat taccgatggc    5880
ggcgcgcgtt ataacttctc cggcgtacag gggatcggta tcgccaacct gagcgattct    5940
ctccatgcgt tgaaagggat ggttttgat caacagcgtt taagttttga cgaattgctg    6000
tcggtattaa aagccaactt tgcaacgcca gaaggcgaaa aagtccgcgc tgcttaatt    6060 aaccgctttg agaaatacgg taacgatatc gacgaggtgg ataacattag cgccgaactg    6120
ttgcgccact actgcaaaga agtggaaaaa taccagaacc cgcgcggcgg ctacttcacg    6180
ccgggatcgt agggcttcaa actttcgccc ctcctggcat tgattcagcc tgtcggaact    6240
ggtatttaac cagactaatt attttgatgc gcgaaattaa tcgttacagg aaaagccaaa    6300
gctgaatcga ttttatgatt tggttcaatt cttcctttag cggcataatg tttaatgacg    6360
tacgaaacgt cagcggtcaa cacccgccag caatggactg tattgcgctc ttcgtgcgtc    6420
gcgtctgtta aaaactggcg ctaacaatac aggctaaagt cgaaccgcca ggctagactt    6480
tagttccaca acactaaacc tataagttgg ggaaatacaa tgttccagca agaagttacc    6540
attaccgctc cgacaatctg ctaatccacg agatgcggcc caatttactg cttaggagaa    6600
gatcatgggt tgttcgata aactgaaatc tctggttccc gacgacaaga aggataccgg    6660
aactattgag atcattgctc cgctctctgg cgagatcgtc aatatcgaag acgtgccgga    6720
tgtcgttttt gcggaaaaaa tcgttggtga tggtattgct atcaaaccaa cgggtaacaa    6780
aatggtcgcg ccagtagacg gcaccattgg taaaatcttt gaaaccaacc acgcattctc    6840
tatcgaatct gatagcggcg ttgaactgtt cgtccacttc ggtatcgaca ccgttgaact    6900
gaaaggcgaa ggcttcaagc gtattgctga agaaggtcag cgcgtgaaag ttggcgatac    6960
tgtcattgaa tttgatctgc cgctgctgga agagaaagcc aagtctaccc tgactccggt    7020
tgttatctcc aacatggacg aaatcaaaga actgatcaaa ctgtccggta gcgtaaccgt    7080
gggtgaaacc ccggttatcc gcatcaagaa gtaattcttg ccgcagtgaa aaatggcgcc    7140
catcggcgcc atttttttat gcttccgcca gcggcggcaa aatcaattca tcgctctcat    7200
gctgctgggt gtagcgccct accgtttctg ctcacgttcc gttgggatcg gtggttggcg    7260
cgacgccaga cggtcgtttt gccggagaac agctggcaga cggcggcttg tcacctatgc    7320
tgggtcagga cgcacaaggg ccaacggcgg tactgaagtc agtcagtaag ctcgataaca    7380
cactgctgtc taacggtaca ttgctgaacg tgaaattcac tccggcgacc ctggaaggtg    7440
aagcgggatt acgcaaactg gccgacttct acgggcgtt tacccagctt aagttacaac    7500
atattcagtt taacgtggtg aacgccgaca cgttgcggga agcgcaacag cgcccacaag    7560
attatgccgg gctggtggtg cgcgttgccg gatacagcgc cttctttgtc gaactgtcga    7620
aggagatcca ggatgacatc atccgccgga cagcgcatca gctgtaacgt tgtggaaacg    7680
cgccgcaatg atgtggcgcg cattttcaac attcagcgtt attcactgaa tgacggtgag    7740
ggcattcgta cggtggtctt ttttaaaggc tgtccgcatc tttgcccgtg gtgtgctaat    7800
ccggagtcga tctccggcaa aatccagacg gtacgcagag aggcgaaatg tctgcactgt    7860
gcgaaatgtt tgcgtgatgc ggatgaatgc ccctccgggg cgtttgaacg gattggtcgc    7920
gatatcagcc ttgacgctct ggaacgggaa gtgatgaaag atgacatttt ttttcgcacg    7980
tccggcggcg gcgtcacgct ttctggcggc gaagtgttaa tgcaggcgga gtttgctacc    8040
```

```
cgttttttac agcgactgca gctgtggggt gtctcatgtg ccattgaaac tgccggagac    8100
gcgccagcca gcaagctgtt accgctggcg aaattgtgcg atgaagtgtt gttcgattta    8160
aaaatcatgg acgcgactca ggcgcgggat gtggtgaaga tgaacctgcc acgcgtgctg    8220
gagaatctgc gtttgctggt gagtgagggc gtcaacgtga tcccgcgttt accgctgatc    8280
cctggtttca cgctcagccg ggagaatatg cagcaggcgc tggatgtgct gatcccgctg    8340
aatatcaggc agatccatct gttaccgttt catcagtacg gcgaaccgaa ataccgcctg    8400
ctggggaaaa catggtcgat gaaagaggtg cctgcgccgt cgtcagccga tgtggcaacg    8460
atgcgcgaaa tggcagaacg ggccggattt caggttaccg tgggaggtta aaatggcata    8520
cctggtggca gtaaccgcct gcgtcagtgg cgtggcgcat acttatatgg cggcggaacg    8580
gctggaaaag ttgtgcctgt tagagaagtg gggagtcagc attgaaactc agggcgctcg    8640
aattcactgg ccgtcgtttt acaacgtcgt gactgggaaa accctggcgt tacccaactt    8700
aatcgccttg cagcacatcc ccctttcgcc agctggcgta atagcgaaga ggcccgcacc    8760
gatcgccctt cccaacagtt gcgcagcctg aatggcgaat ggcgcctgat gcggtatttt    8820
ctccttacgc atctgtgcgg tatttcacac cgcatatggt gcactctcag tacaatctgc    8880
tctgatgccg catagttaag ccagccccga cacccgccaa cacccgctga cgaattc      8937
```

<210> SEQ ID NO 9
<211> LENGTH: 23
<212> TYPE: DNA
<213> ORGANISM: Artificial Sequence
<220> FEATURE:
<223> OTHER INFORMATION: PCR primer BY124 for amplifying and cloning teh pflDC geen of Escherichia coli C, or cassettes embedded in pflD, together with BY125.

<400> SEQUENCE: 9
tgccaatacc cgtgaaatct cgc                                              23

<210> SEQ ID NO 10
<211> LENGTH: 23
<212> TYPE: DNA
<213> ORGANISM: Artificial Sequence
<220> FEATURE:
<223> OTHER INFORMATION: PCR Primer BY125 for amplifying and cloning the pflDC genes of E. coli C, or cassettes embedded in pflD, together with BY124.

<400> SEQUENCE: 10
cgccctgagt ttcaatgctg act                                              23

<210> SEQ ID NO 11
<211> LENGTH: 26
<212> TYPE: DNA
<213> ORGANISM: Artificial Sequence
<220> FEATURE:
<223> OTHER INFORMATION: PCR primer AC74 for amplifying and clonig the tdcC-tdcG region of E. coli C and derivatives or cassettes embedded in teh tdcC-tdcG region,together with AC75.

<400> SEQUENCE: 11
tgagctacct ggtatggccg tttatc                                           26

<210> SEQ ID NO 12
<211> LENGTH: 22
<212> TYPE: DNA
<213> ORGANISM: Artificial Sequence
<220> FEATURE:
<223> OTHER INFORMATION: PCR primer Ac75 for amplifying and cloning the

```
tdcC-tdcG region of E. coli C and derivatives, or cassettes
embedded in teh tdcC-tdcG region, together with AC74.

<400> SEQUENCE: 12
cccgccgccg acagagtaat ag                                        22
```

What is claimed is:

1. An *Escherichia coli* bacterium, which produces more than 30 g/L of a succinic acid in 48 hours when grown in a minimal medium, wherein a biosynthetic intermediate for said succinic acid is phosphoenolpyruvate, and said *Escherichia coli* bacterium comprises:
- at least one exogenous gene that encodes a protein that functions in the facilitated diffusion of a sugar,
- a mutation or deletion in one or more genes that encode one or more proteins that function in a phosphotransferase system for sugar import, and
- at least one additional copy of a gene that encodes a Crr protein that functions in catabolite repression.

2. The *Escherichia coli* bacterium of claim 1, further comprising a deletion in a gene that encodes a sugar importer that functions using proton symport.

3. The *Escherichia coli* bacterium of claim 1, wherein said one or more genes comprise a ptsH gene.

4. The *Escherichia coli* bacterium of claim 1, wherein said one or more genes comprise a ptsI gene.

5. The *Escherichia coli* bacterium of claim 1, wherein said one or more genes comprise a gene selected from the group consisting of a ptsH gene, and a ptsI gene.

6. The *Escherichia coli* bacterium of claim 1, wherein said at least one exogenous gene is a glf gene.

7. The *Escherichia coli* bacterium of claim 1, wherein said at least one exogenous gene is a glf gene and a glk gene.

8. The *Escherichia coli* bacterium of claim 1, wherein said at least one exogenous gene is a glf gene and a frk gene.

9. The *Escherichia coli* bacterium of claim 2, wherein said gene is a galP gene.

10. A method of producing succinic acid, the method comprising:
- growing the *Escherichia coli* bacterium of claim 1 in a minimal medium, to produce succinic acid; and
- optionally purifying said succinic acid from the minimal medium.

11. The method of claim 10, wherein the *Escherichia coli* bacterium produces, in 48 hours, at least 60 g/L of succinic acid and 4.2 g/L or less of acetate.

12. The method of claim 10, wherein the growing is microaerobic.

13. The *Escherichia coli* bacterium of claim 1, wherein said at least one additional copy is integrated at a locus separate from a native crr locus.

* * * * *